US007205456B2

(12) United States Patent
Hallahan et al.

(10) Patent No.: US 7,205,456 B2
(45) Date of Patent: Apr. 17, 2007

(54) *CIS*-PRENYLTRANSFERASES FROM THE RUBBER-PRODUCING PLANTS RUSSIAN DANDELION (*TARAXACUM KOK-SAGHYZ*) AND SUNFLOWER (*HELIANTHUS ANNUS*)

(75) Inventors: David L. Hallahan, Wilmington, DE (US); Natalie M. Keiper-Hrynko, Bear, DE (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 112 days.

(21) Appl. No.: 10/532,013

(22) PCT Filed: Nov. 12, 2003

(86) PCT No.: PCT/US03/36164

§ 371 (c)(1),
(2), (4) Date: Apr. 20, 2005

(87) PCT Pub. No.: WO2004/044173

PCT Pub. Date: May 27, 2004

(65) Prior Publication Data

US 2006/0225144 A1   Oct. 5, 2006

(51) Int. Cl.
*A01H 1/00* (2006.01)
*C07H 21/04* (2006.01)
*C07K 14/415* (2006.01)
*C12N 5/14* (2006.01)
*C12N 9/00* (2006.01)

(52) U.S. Cl. .................. 800/295; 435/6; 435/69.1; 435/468; 435/419; 435/252.3; 435/320.1; 435/183; 530/370; 536/23.6; 800/278

(58) Field of Classification Search .............. 435/6, 435/69.1, 468, 419, 252.3, 320.1, 183; 530/370; 536/23.6; 800/278
See application file for complete search history.

(56) References Cited

FOREIGN PATENT DOCUMENTS

WO    WO 01/21650 A2   3/2001

OTHER PUBLICATIONS

Lin et al., Nature, vol. 402, pp. 761-768, 1999.*
Melinda N. Martin, The Latex of *Hevea brasiliensis* Contains High Levels of Both Chitinases and Chitinases/Lysozymes1, Plant Physiol., vol. 95:469-476, 1991.
Takeshi Yagami et al., Plant defense-related enzymes as latex antigens, Journal of Allergy and Clinical Immunology, vol. 101(3):379-385, 1998.
Ralph A. Backhaus, Rubber Formation in Plants—A Mini-Review, Israel Journal of Botany, vol. 34:283-293, 1985.
Joseph Chappell, Biochemistry and Molecular Biology of the Isoprenoid Biosynthetic Pathway in Plants, Annu. Rev. Plant Physiol., Plant Mol. Biol., vol. 46:521-547, 1995.
Thomas Meeker, Low Molecular Weight Polyisoprenes Offer Versatility in Bonding Techniques, Adhesives Age, vol. 41(7):23-26, 1998.
National Center for Biotechnology Information General Identifier No. 22213620, Accession No. AY124934, Aug. 13, 2002, C. Coldren et al., *Cis*-prenyltransferases from Plants.
National Center for Biotechnology Information General Identifier No. 22213604, Accession No. AY124474, Aug. 13, 2002, C. Coldren et al., *Cis*-prenyltransferases from plants.
National Center for Biotechnology Information General Identifier No. 22213602, Accession No. AY124473, Aug. 13, 2002, C. Coldren et al., *Cis*-prenyltransferases from plants.
National Center for Biotechnology Information General Identifier No. 22213600, Accession No. AY124472, Aug. 13, 2002, C. Coldren et al., *Cis*-prenyltransferases from plants.
National Center for Biotechnology Information General Identifier No. 22213598, Accession No. AY124471, Aug. 13, 2002, C. Coldren et al., *Cis*-prenyltransferases from plants.
National Center for Biotechnology Information General Identifier No. 22213596, Accession No. AY124470, Aug. 13, 2002, C. Coldren et al., *Cis*-prenyltransferases from plants.
National Center for Biotechnology Information General Identifier No. 22213594, Accession No. AY124469, Aug. 13, 2002, C. Coldren et al., *Cis*-prenyltransferases from plants.
National Center for Biotechnology Information General Identifier No. 22213592, Accession No. AY124468, Aug. 13, 2002, C. Coldren et al., *Cis*-prenyltransferases from plants.
National Center for Biotechnology Information General Identifier No. 22213590, Accession No. AY124467, Aug. 13, 2002, C. Coldren et al., *Cis*-prenyltransferases from plants.
National Center for Biotechnology Information General Identifier No. 22213588, Accession No. AY124466, Aug. 13, 2002, C. Coldren et al., *Cis*-prenyltransferases from plants.
National Center for Biotechnology Information General Identifier No. 22213586, Accession No. AY124465, Aug. 13, 2002, C. Coldren et al., *Cis*-prenyltransferases from plants.
National Center for Biotechnology Information General Identifier No. 22213584, Accession No. AY124464, Aug. 13, 2002, C. Coldren et al., *Cis*-prenyltransferases from plants.
National Center for Biotechnology Information General Identifier No. 20387100, Accession No. AB061236, May 2, 2002, K. Asawatreratanakul et al., Molecular cloning, expression and characterization of *Cis*-prenyltransferases from *Hevea brasiliensis*.
National Center for Biotechnology Information General Identifier No. 20563021, Accession No. AB074307, Sep. 18, 2002, T. Sando et al., Characterization of *Cis*-prenyltransferase of *Hevea brasiliensis*.
Christian M. Apfel et al., Use of Genomics To Identify Bacterial Undecaprenyl Pyrophosphate Synthetase: Cloning, Expression, and Characterization of the Essential uppS Gene, Journal of Bacteriology, vol. 181(2):483-492, 1999.

(Continued)

Primary Examiner—Phuong T. Bui

(57) ABSTRACT

This invention pertains to nucleic acid fragments encoding plant cis-prenyltransferases. More specifically, this invention pertains to a cis-prenyltransferase homolog from latex of the rubber-producing plant species *Taraxacum kok-saghyz* (russian dandelion) and a cis-prenyltransferase homolog from the rubber-producing plant species *Helianthus annus* (sunflower).

8 Claims, 2 Drawing Sheets

OTHER PUBLICATIONS

Naoto Shimizu et al., Molecular Cloning, Expression, and Purification of Undecaprenyl Diphosphate Synthase, The Journal of Biological Chemistry, vol. 273(31):19476-19481, 1998.

Hussin Mohd Nor et al., Telechelic Liquid Natural Rubber: A Review, Prog. Polym. Sci., vol. 23:143-177, 1998.

Katrina Cornish, Similarities and differences in rubber biochemistry among plant species, Phytochemistry, vol. 57:1123-1134, 2001.

Douglas J. McGarvey et al., Terpenoid Metabolism, The Plant Cell, vol. 7:1015-1026, 1995.

National Center for Biotechnology Information General Identifier No. 20387098, Accession No. AB061235, May 2, 2002, K. Asawatreratanakul et al., Molecular cloning, expression and characterization of cis-prenyltransferases from *Hevea brasiliensis*.

National Center for Biotechnology Information General Identifier No. 16904643, Accession No. AB061237, Nov. 13, 2001, K. Asawatreratanakul et al., Molecular cloning, expression and characterization of cis-prenyltransferases from *Hevea brasiliensis*.

* cited by examiner

Figure 1

SEQUENCE LISTING

<160> NUMBER OF SEQ ID NOS: 45

<210> SEQ ID NO 1
<211> LENGTH: 746
<212> TYPE: DNA
<213> ORGANISM: Taraxacum kok-saghyz

<400> SEQUENCE: 1

```
gatcgaaggc tttctgaaag aagttagtat tataaaccaa tatggcgtta gagtcttgtt      60
catcggtgat ctcgataggt tatatgagcc cgtaaggatt gctgctgaga aggccatgga     120
agccaccgct aaaaactcaa ccacatatct cctcgtatgt gttgcttaca cttcttccca     180
tgaaatccca cgtgccatcc acgaagcttg tgaagaaagc atacgggtca tgaacggaaa     240
cgggtttttc aatggaagcg atataccaa cgtgaatcat ggaagtcagg cggtgatcaa      300
agtggtggat cttgataagc atatgtacat ggggtggca ccggatcctg atattttagt      360
aaggagctcc ggcgaaacaa ggctgagcaa ctttctgctg tggcagacca ccaactgttt     420
gttgtattcc ccgaaagctt tgtggccgga gatggggttc tggcaggtgg tttggggaat     480
cttggagttt caaaacaatt ataattactt ggagaagaag aagaagcagg cgtaaggatg     540
tgttcaaaaa gtaaggtaat ctgtctttaa atgagtttgg agtgtgctgt gagcattaat     600
gggattttc ttcccaatat gaactttcaa ttttgggtcg attataatat atgatccata      660
tgtatatgaa cgttgtgtga tgcattatac gagcagaaga acgttgtatt tttactaaaa     720
aaaaaaaaaa aaaaaaaaaa aaaaaa                                          746
```

<210> SEQ ID NO 2
<211> LENGTH: 788
<212> TYPE: DNA
<213> ORGANISM: Taraxacum kok-saghyz

<400> SEQUENCE: 2

```
gcccttcgcg gatccagacg ctgcgtttgc tggctttgat gaaaataatc tattccacca      60
agttatctct ctctctctct ctctctctct ctctctctct ctctctgtct gtctctcttc     120
ctctgtctct ctagtataca attggcaaat aggattaagc cggctcattt gttaaaccaa     180
gatgcaagtg aatccaatca ttactacaga tagttcactg aaactagtgg aagaagaaag     240
atcaaatggt aggatcggca atttcttagg aggcttaaac gccaccttaa gaaaactcgt     300
gtttcgtgtc attgcttctc gcccaatccc agaacacatc gccttcatcc tcgatggaaa     360
ccgaaggttc gccaggaaat ggaacctcac agaaggcgcc ggccacaaaa ccggcttcct     420
agcactcatg tcggtcctca aatactgcta cgagatcgga gttaagtacg tcaccatcta     480
cgccttcagc ctcgacaatt tcaatcgacg ccctgatgaa gtccagtacg tcatggactt     540
gatgcaagac aagatcgaag ctttctgaa agaagttagt attataaacc aatatggcgt      600
tagagtcttg ttcatcggtg atctcgatag gttatatgag cccgtaagga ttgctgctga     660
gaaggccatg gaagccaccg ctaaaaactc aaccacatat ctcctcgtat gtgttgctta     720
cacttcttcc catgaaatcc cacgtgccat ccacgaagct tgtgaagaaa gcatacgggt     780
catgaacg                                                              788
```

<210> SEQ ID NO 3
<211> LENGTH: 906
<212> TYPE: DNA
<213> ORGANISM: Taraxacum kok-saghyz

<400> SEQUENCE: 3

```
atgcaagtga atccaatcat tactacagat agttcactga aactagtgga agaagaaaga      60
tcaaatggta ggatcggcaa tttcttagga ggcttaaacg ccaccttaag aaaactcgtg     120
tttcgtgtca ttgcttctcg cccaatccca gaacacatcg ccttcatcct cgatggaaac     180
cgaaggttcg ccaggaaatg gaacctcaca gaaggcgccg gccacaaaac cggcttccta     240
gcactcatgt cggtcctcaa atactgctac gagatcggag ttaagtacgt caccatctac     300
gccttcagcc tcgacaattt caatcgacgc cctgatgaag tccagtacgt catggacttg     360
atgcaagaca gatcgaagg ctttctgaaa gaagttagta ttataaacca atatggcgtt      420
agagtcttgt tcatcggtga tctcgatagg ttatatgagc ccgtaaggat tgctgctgag     480
aaggccatgg aagccaccgc taaaaactca accacatatc tcctcgtatg tgttgcttac     540
acttcttccc atgaaatccc acgtgccatc cacgaagctt gtgaagaaag catacgggtc     600
atgaacggaa acgggttttt caatggaagc ggatatacca acgtgaatca tggaagtcag     660
gcggtgatca aagtggtgga tcttgataag catatgtaca tggggtggc accggatcct      720
gatattttag taaggagctc cggcgaaaca aggctgagca acttctgct gtggcagacc      780
accaactgtt tgttgtattc cccgaaagct tgtggccgg agatgggtt ctggcaggtg       840
gtttggggaa tcttggagtt tcaaaacaat ataattact tggagaagaa gaagaagcag      900
gcgtaa                                                                906
```

<210> SEQ ID NO 4
<211> LENGTH: 301
<212> TYPE: PRT
<213> ORGANISM: Taraxacum kok-saghyz

<400> SEQUENCE: 4

```
Met Gln Val Asn Pro Ile Ile Thr Thr Asp Ser Ser Leu Lys Leu Val
1               5                   10                  15

Glu Glu Glu Arg Ser Asn Gly Arg Ile Gly Asn Phe Leu Gly Gly Leu
            20                  25                  30

Asn Ala Thr Leu Arg Lys Leu Val Phe Arg Val Ile Ala Ser Arg Pro
        35                  40                  45

Ile Pro Glu His Ile Ala Phe Ile Leu Asp Gly Asn Arg Arg Phe Ala
    50                  55                  60

Arg Lys Trp Asn Leu Thr Glu Gly Ala Gly His Lys Thr Gly Phe Leu
65                  70                  75                  80

Ala Leu Met Ser Val Leu Lys Tyr Cys Tyr Glu Ile Gly Val Lys Tyr
                85                  90                  95

Val Thr Ile Tyr Ala Phe Ser Leu Asp Asn Phe Asn Arg Arg Pro Asp
            100                 105                 110

Glu Val Gln Tyr Val Met Asp Leu Met Gln Asp Lys Ile Glu Gly Phe
        115                 120                 125

Leu Lys Glu Val Ser Ile Ile Asn Gln Tyr Gly Val Arg Val Leu Phe
    130                 135                 140

Ile Gly Asp Leu Asp Arg Leu Tyr Glu Pro Val Arg Ile Ala Ala Glu
145                 150                 155                 160

Lys Ala Met Glu Ala Thr Ala Lys Asn Ser Thr Thr Tyr Leu Leu Val
                165                 170                 175

Cys Val Ala Tyr Thr Ser Ser His Glu Ile Pro Arg Ala Ile His Glu
            180                 185                 190
```

```
Ala Cys Glu Glu Ser Ile Arg Val Met Asn Gly Asn Gly Phe Phe Asn
        195                 200                 205

Gly Ser Gly Tyr Thr Asn Val Asn His Gly Ser Gln Ala Val Ile Lys
    210                 215                 220

Val Val Asp Leu Asp Lys His Met Tyr Met Gly Val Ala Pro Asp Pro
225                 230                 235                 240

Asp Ile Leu Val Arg Ser Ser Gly Glu Thr Arg Leu Ser Asn Phe Leu
                245                 250                 255

Leu Trp Gln Thr Thr Asn Cys Leu Leu Tyr Ser Pro Lys Ala Leu Trp
            260                 265                 270

Pro Glu Met Gly Phe Trp Gln Val Val Trp Gly Ile Leu Glu Phe Gln
        275                 280                 285

Asn Asn Tyr Asn Tyr Leu Glu Lys Lys Lys Gln Ala
    290                 295                 300

<210> SEQ ID NO 5
<211> LENGTH: 505
<212> TYPE: DNA
<213> ORGANISM: Helianthus annus

<400> SEQUENCE: 5
accagaaaga ttgaagggtt tatgaaagaa ttaacaattg tgaacaggta tggtgttaga      60
gtcttgttta tcggcgatct taaaaggtta tacgagcccg ttagagttgc agccgagaaa     120
gcaatggagg ccactgctaa caacacacat acatatcttt tagtatgtgt tgcttacact     180
tcttcacacg aaatcccgcg tgccgtttat gaatcttgcg aagaaaagag tggtggaacc     240
ggagttatga ttaatggaaa tggaagtgtg aacggagatt acagtgaaga aaagagtggt     300
ggaaccggag ttatggtgaa tggaaatggg agtgtgaatg gagattacag taatggagat     360
catgaggagg gggttaaagt ggtggatatt gacaaacata tgtatatggc agtggctcct     420
gatcctgata ttttggtcag gagctcaggg gagacgaggt tgagtaactt tttgctgtgg     480
caaaccacca actgcgtgtt gtatt                                          505

<210> SEQ ID NO 6
<211> LENGTH: 168
<212> TYPE: PRT
<213> ORGANISM: Helianthus annus

<400> SEQUENCE: 6

Thr Arg Lys Ile Glu Gly Phe Met Lys Glu Leu Thr Ile Val Asn Arg
1               5                   10                  15

Tyr Gly Val Arg Val Leu Phe Ile Gly Asp Leu Lys Arg Leu Tyr Glu
            20                  25                  30

Pro Val Arg Val Ala Ala Glu Lys Ala Met Glu Ala Thr Ala Asn Asn
        35                  40                  45

Thr His Thr Tyr Leu Leu Val Cys Val Ala Tyr Thr Ser Ser His Glu
    50                  55                  60

Ile Pro Arg Ala Val Tyr Glu Ser Cys Glu Glu Lys Ser Gly Gly Thr
65                  70                  75                  80

Gly Val Met Ile Asn Gly Asn Gly Ser Val Asn Gly Asp Tyr Ser Glu
                85                  90                  95

Glu Lys Ser Gly Gly Thr Gly Val Met Val Asn Gly Asn Gly Ser Val
            100                 105                 110

Asn Gly Asp Tyr Ser Asn Gly Asp His Glu Glu Gly Val Lys Val Val
        115                 120                 125
```

```
Asp Ile Asp Lys His Met Tyr Met Ala Val Ala Pro Asp Pro Asp Ile
        130                 135                 140

Leu Val Arg Ser Ser Gly Glu Thr Arg Leu Ser Asn Phe Leu Leu Trp
145                 150                 155                 160

Gln Thr Thr Asn Cys Val Leu Tyr
                165

<210> SEQ ID NO 7
<211> LENGTH: 228
<212> TYPE: PRT
<213> ORGANISM: Calendula officinalis

<400> SEQUENCE: 7

Met Pro Lys His Val Ala Phe Ile Met Asp Gly Asn Arg Arg Trp Ala
1               5                   10                  15

Val Glu Lys Gly Trp Ser Pro Met Thr Gly His Ser Ala Met Arg Lys
                20                  25                  30

Thr Leu Gln Ser Leu Leu Phe Arg Cys Ser Lys Phe Lys Ile Lys Ala
            35                  40                  45

Val Ser Ile Tyr Ala Phe Ser Thr Glu Asn Trp Thr Arg Pro Lys Glu
50                  55                  60

Glu Val Asp Phe Leu Met Glu Met Tyr Glu Asp Leu Leu Arg Thr Asp
65                  70                  75                  80

Ala Glu Glu Leu Leu Ser Leu Gly Cys Arg Val Ser Ile Met Gly Lys
                85                  90                  95

Lys Thr Asn Leu Pro Lys Ser Leu Gln Lys Leu Cys Ile Glu Ile Glu
            100                 105                 110

Glu Lys Ser Arg Ala Asn Ser Gly Thr His Val Asn Tyr Ala Leu Asn
        115                 120                 125

Tyr Ser Gly Lys Tyr Asp Ile Ile Glu Ala Cys Lys Ser Val Ala Thr
    130                 135                 140

Lys Val Lys Asp Gly Val Ile Ile Pro Lys Gln Ile Asp Glu Lys Tyr
145                 150                 155                 160

Phe Lys Gln Glu Leu Gly Thr Lys Met Ile Asp Phe Pro Tyr Pro Asp
                165                 170                 175

Leu Val Ile Arg Thr Ser Gly Glu Ile Arg Leu Ser Asn Phe Met Leu
            180                 185                 190

Trp Gln Met Ala Tyr Ser Glu Leu Tyr Phe Thr Asp Lys Tyr Phe Pro
        195                 200                 205

Asp Phe Gly Glu Asn Asp Leu Ile Glu Ala Leu Leu Ala Phe Gln Lys
    210                 215                 220

Val Arg Lys Cys
225

<210> SEQ ID NO 8
<211> LENGTH: 290
<212> TYPE: PRT
<213> ORGANISM: Hevea brasiliensis

<400> SEQUENCE: 8

Met Glu Leu Tyr Asn Gly Glu Arg Pro Ser Val Phe Arg Leu Leu Gly
1               5                   10                  15

Lys Tyr Met Arg Lys Gly Leu Tyr Ser Ile Leu Thr Gln Gly Pro Ile
            20                  25                  30

Pro Thr His Ile Ala Phe Ile Leu Asp Gly Asn Arg Arg Phe Ala Lys
        35                  40                  45
```

```
Lys His Lys Leu Pro Glu Gly Gly His Lys Ala Gly Phe Leu Ala
     50                  55                  60

Leu Leu Asn Val Leu Thr Tyr Cys Tyr Glu Leu Gly Val Lys Tyr Ala
 65                  70                  75                  80

Thr Ile Tyr Ala Phe Ser Ile Asp Asn Phe Arg Arg Lys Pro His Glu
                 85                  90                  95

Val Gln Tyr Val Met Asp Leu Met Leu Glu Lys Ile Glu Gly Met Ile
             100                 105                 110

Met Glu Glu Ser Ile Ile Asn Ala Tyr Asp Ile Cys Val Arg Phe Val
         115                 120                 125

Gly Asn Leu Lys Leu Leu Ser Glu Pro Val Lys Thr Ala Ala Asp Lys
     130                 135                 140

Ile Met Arg Ala Thr Ala Asn Asn Ser Lys Cys Val Leu Leu Ile Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
            180                 185                 190

Ala Asn Ala Thr Gly Ser Ser Thr Val Ile Gln Thr Glu Asn Met Glu
        195                 200                 205

Ser Tyr Ser Gly Ile Lys Leu Val Asp Leu Lys Asn Thr Tyr Ile
    210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

Tyr Ala Leu Trp Pro Glu Ile Gly Leu Arg His Val Val Trp Ser Val
            260                 265                 270

Ile Asn Phe Gln Arg His Tyr Ser Tyr Leu Glu Lys His Lys Glu Tyr
        275                 280                 285

Leu Lys
    290

<210> SEQ ID NO 9
<211> LENGTH: 290
<212> TYPE: PRT
<213> ORGANISM: Hevea brasiliensis

<400> SEQUENCE: 9

Met Glu Leu Tyr Asn Gly Glu Arg Pro Ser Val Phe Arg Leu Leu Glu
 1               5                  10                  15

Lys Tyr Met Arg Lys Gly Leu Tyr Ser Ile Leu Thr Gln Gly Pro Ile
             20                  25                  30

Pro Thr His Ile Ala Phe Ile Leu Asp Gly Asn Arg Arg Phe Ala Lys
         35                  40                  45

Lys His Lys Leu Pro Glu Gly Gly His Lys Ala Gly Phe Leu Ala
     50                  55                  60

Leu Leu Asn Val Leu Thr Tyr Cys Tyr Glu Leu Gly Val Lys Tyr Ala
 65                  70                  75                  80

Thr Ile Tyr Ala Phe Ser Ile Asp Asn Phe Arg Arg Lys Pro His Glu
                 85                  90                  95

Val Gln Tyr Val Met Asp Leu Met Leu Glu Lys Ile Glu Gly Met Ile
             100                 105                 110

Met Glu Glu Ser Ile Ile Asn Ala Tyr Asp Ile Cys Val Arg Phe Val
         115                 120                 125
```

-continued

```
Gly Asn Leu Lys Leu Leu Ser Glu Pro Val Lys Thr Ala Ala Asp Lys
    130                 135                 140

Ile Met Arg Ala Thr Ala Asn Asn Ser Lys Cys Val Leu Leu Ile Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
            180                 185                 190

Ala Asn Ala Thr Gly Ser Ser Thr Val Ile Gln Thr Glu Asn Met Glu
        195                 200                 205

Ser Tyr Ser Gly Ile Lys Leu Val Asp Leu Glu Lys Asn Thr Tyr Ile
    210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

Tyr Ala Leu Trp Pro Glu Ile Gly Leu Arg His Val Val Trp Ser Val
            260                 265                 270

Ile Asn Phe Gln Arg His Tyr Ser Tyr Leu Glu Lys His Lys Glu Tyr
        275                 280                 285

Leu Lys
    290

<210> SEQ ID NO 10
<211> LENGTH: 296
<212> TYPE: PRT
<213> ORGANISM: Hevea brasiliensis

<400> SEQUENCE: 10

Met Glu Ile Tyr Thr Gly Gln Arg Pro Ser Val Phe Arg Ile Phe Gly
1               5                   10                  15

Lys Tyr Met Arg Lys Gly Leu Tyr Ser Ile Leu Thr Gln Gly Pro Ile
            20                  25                  30

Pro Thr His Leu Ala Phe Ile Met Asp Gly Asn Arg Arg Phe Ala Lys
        35                  40                  45

Lys His Lys Met Lys Glu Ala Glu Gly Tyr Lys Ala Gly Tyr Leu Ala
    50                  55                  60

Leu Leu Arg Thr Leu Thr Tyr Cys Tyr Glu Leu Gly Val Arg Tyr Val
65                  70                  75                  80

Thr Ile Tyr Ala Phe Ser Ile Asp Asn Phe Arg Arg Gln Pro Arg Glu
                85                  90                  95

Val Gln Cys Val Met Asn Leu Met Met Glu Lys Ile Glu Glu Ile Ile
            100                 105                 110

Val Glu Glu Ser Ile Met Asn Ala Tyr Asp Val Gly Val Arg Ile Val
        115                 120                 125

Gly Asn Leu Asn Leu Leu Asp Glu Pro Ile Arg Ile Ala Ala Glu Lys
    130                 135                 140

Ile Met Arg Ala Thr Ala Asn Asn Ser Gly Phe Val Leu Leu Ile Ala
145                 150                 155                 160

Val Ala Tyr Ser Ser Thr Asp Glu Ile Gly His Ala Val Glu Glu Ser
                165                 170                 175

Ser Lys Asp Lys Leu Asn Ser Asn Glu Val Cys Asn Asn Gly Ile Glu
            180                 185                 190

Ala Glu Gln Glu Phe Lys Glu Ala Asn Gly Thr Gly Asn Ser Val Ile
```

```
                195                 200                 205
Pro Val Gln Lys Thr Glu Ser Tyr Ser Gly Ile Asn Leu Ala Asp Leu
        210                 215                 220

Glu Lys Asn Thr Tyr Val Asn Pro His Pro Asp Val Leu Ile Arg Thr
225                 230                 235                 240

Ser Gly Leu Ser Arg Leu Ser Asn Tyr Leu Leu Trp Gln Thr Ser Asn
            245                 250                 255

Cys Ile Leu Tyr Ser Pro Phe Ala Leu Trp Pro Glu Ile Gly Leu Arg
                260                 265                 270

His Leu Val Trp Thr Val Met Asn Phe Gln Arg His His Ser Tyr Leu
            275                 280                 285

Glu Lys His Lys Glu Tyr Leu Lys
        290                 295

<210> SEQ ID NO 11
<211> LENGTH: 309
<212> TYPE: PRT
<213> ORGANISM: Vitis sp.

<400> SEQUENCE: 11

Met Leu Ser Phe Arg Phe Pro Ile Ser Ala Asp Asn Ala Arg His Thr
1               5                   10                  15

Phe Lys Ser Lys His Ser Ser Cys Thr Phe Arg Ser Asn Arg Ile Asp
            20                  25                  30

Ser Phe Ser Phe Pro Pro Ile Ser Val Pro Arg Phe His Lys Leu Arg
        35                  40                  45

Thr Ala Lys Thr Asp Val Val Gly Glu Glu Ala Arg Glu Val Asn
    50                  55                  60

Glu Arg Ala Glu Glu Phe Pro Asp Gly Leu Arg Arg Glu Leu Met Pro
65                  70                  75                  80

Glu His Val Ala Val Ile Met Asp Gly Asn Val Arg Trp Ala Gln Lys
                85                  90                  95

Arg Gly Leu Pro Ala Ala Ser Gly His Gln Ala Gly Val Arg Ser Leu
            100                 105                 110

Arg Glu Leu Val Glu Leu Cys Cys Lys Trp Gly Ile Lys Val Leu Ser
        115                 120                 125

Val Phe Ala Phe Ser Tyr Asp Asn Trp Ser Arg Ser Glu Gly Glu Val
    130                 135                 140

Gly Phe Leu Met Ser Leu Ile Glu Arg Val Lys Ala Glu Leu Pro
145                 150                 155                 160

Ile Leu Gly Gly Lys Ala Phe Glu Cys Arg Asp Trp Gly Phe Val Lys
                165                 170                 175

Ala Ser Glu Gln Leu Gln Leu Ile Ile Asp Val Glu Glu Thr Thr Lys
            180                 185                 190

Glu Asn Ser Arg Leu Gln Phe Ile Val Ala Leu Ser Tyr Ser Gly Gln
        195                 200                 205

Cys Asp Ile Leu Gln Ala Cys Lys Asn Ile Gly His Lys Val Lys Asp
    210                 215                 220

Gly Leu Ile Glu Pro Glu Asp Ile Asn Lys Ser Leu Ile Glu Gln Glu
225                 230                 235                 240

Leu Gln Thr Asn Cys Thr Glu Phe Pro Phe Pro Asp Leu Leu Ile Arg
                245                 250                 255

Thr Ser Gly Glu Leu Arg Val Ser Asn Phe Met Leu Trp Gln Ile Ala
            260                 265                 270
```

Tyr Thr Glu Leu Cys Phe Phe Ser Thr Leu Trp Pro Asp Phe Gly Lys
        275                 280                 285

Asp Glu Phe Val Glu Ala Leu Ser Ser Phe Gln Lys Arg Gln Arg Arg
    290                 295                 300

Tyr Gly Gly Arg Asn
305

<210> SEQ ID NO 12
<211> LENGTH: 252
<212> TYPE: PRT
<213> ORGANISM: Oryza sativa

<400> SEQUENCE: 12

Met Pro Lys His Ile Ala Phe Ile Met Asp Gly Asn Arg Arg Tyr Ala
1               5                   10                  15

Lys Phe Arg Ser Ile Gln Glu Gly Ser Gly His Arg Val Gly Phe Ser
            20                  25                  30

Ala Leu Ile Ala Ser Leu Leu Tyr Cys Tyr Glu Met Gly Val Lys Tyr
        35                  40                  45

Ile Thr Val Tyr Ala Phe Ser Ile Asp Asn Phe Lys Arg Asp Pro Thr
    50                  55                  60

Glu Val Lys Ser Leu Met Glu Leu Met Glu Glu Lys Ile Asn Glu Leu
65                  70                  75                  80

Leu Glu Asn Arg Asn Val Ile Asn Lys Val Asn Cys Lys Ile Asn Phe
                85                  90                  95

Trp Gly Asn Leu Asp Met Leu Ser Lys Ser Val Arg Val Ala Ala Glu
            100                 105                 110

Lys Leu Met Ala Thr Thr Ala Glu Asn Thr Gly Leu Val Phe Ser Val
        115                 120                 125

Cys Met Pro Tyr Asn Ser Thr Ser Glu Ile Val Asn Ala Val Asn Lys
    130                 135                 140

Val Cys Ala Glu Arg Arg Asp Ile Leu Gln Arg Glu Asp Ala Asp Ser
145                 150                 155                 160

Val Ala Asn Asn Gly Val Tyr Ser Asp Ile Ser Val Ala Asp Leu Asp
                165                 170                 175

Arg His Met Tyr Ser Ala Gly Cys Pro Asp Pro Asp Ile Val Ile Arg
            180                 185                 190

Thr Ser Gly Glu Thr Arg Leu Ser Asn Phe Leu Leu Trp Gln Thr Thr
        195                 200                 205

Phe Ser His Leu Gln Asn Pro Asp Pro Leu Trp Pro Glu Phe Ser Phe
    210                 215                 220

Lys His Leu Val Trp Ala Ile Leu Gln Tyr Gln Arg Val His Pro Ser
225                 230                 235                 240

Ile Glu Gln Ser Arg Asn Leu Ala Lys Lys Gln Leu
                245                 250

<210> SEQ ID NO 13
<211> LENGTH: 299
<212> TYPE: PRT
<213> ORGANISM: Oryza sativa

<400> SEQUENCE: 13

Met Leu Gly Ser Leu Met Ser Tyr Leu Pro Ser Val Asp Ser Lys Thr
1               5                   10                  15

Glu Asn Thr Asp Glu Leu Ile Ala Thr Gly Val Leu Ala Ser Leu Gln
            20                  25                  30

```
Asn Phe Ile Arg Lys Cys Ile Val Ala Val Leu Ser Tyr Gly Pro Met
            35                  40                  45

Pro Lys His Ile Ala Phe Ile Met Asp Gly Asn Arg Arg Tyr Ala Lys
    50                  55                  60

Phe Arg Ser Ile Gln Glu Gly Ser Gly His Arg Val Gly Phe Ser Ala
65                  70                  75                  80

Leu Ile Ala Ser Leu Leu Tyr Cys Tyr Glu Met Gly Val Lys Tyr Ile
                85                  90                  95

Thr Val Tyr Ala Phe Ser Ile Asp Asn Phe Lys Arg Asp Pro Thr Glu
            100                 105                 110

Val Lys Ser Leu Met Glu Leu Glu Glu Lys Ile Asn Glu Leu Leu
            115                 120                 125

Glu Asn Arg Asn Val Ile Asn Lys Val Asn Cys Lys Ile Asn Phe Trp
    130                 135                 140

Gly Asn Leu Asp Met Leu Ser Lys Ser Val Arg Val Ala Ala Glu Lys
145                 150                 155                 160

Leu Met Ala Thr Thr Ala Glu Asn Thr Gly Leu Val Phe Ser Val Cys
                165                 170                 175

Met Pro Tyr Asn Ser Thr Ser Glu Ile Val Asn Ala Val Asn Lys Val
            180                 185                 190

Cys Ala Glu Arg Arg Asp Ile Leu Gln Arg Glu Asp Ala Asp Ser Val
        195                 200                 205

Ala Asn Asn Gly Val Tyr Ser Asp Ile Ser Val Ala Asp Leu Asp Arg
    210                 215                 220

His Met Tyr Ser Ala Gly Cys Pro Asp Pro Asp Ile Val Ile Arg Thr
225                 230                 235                 240

Ser Gly Glu Thr Arg Leu Ser Asn Phe Leu Leu Trp Gln Thr Thr Phe
                245                 250                 255

Ser His Leu Gln Asn Pro Asp Pro Leu Trp Pro Glu Phe Ser Phe Lys
            260                 265                 270

His Leu Val Trp Ala Ile Leu Gln Tyr Gln Arg Val His Pro Ser Ile
        275                 280                 285

Glu Gln Ser Arg Asn Leu Ala Lys Lys Gln Leu
    290                 295

<210> SEQ ID NO 14
<211> LENGTH: 322
<212> TYPE: PRT
<213> ORGANISM: Glycine max

<400> SEQUENCE: 14

Met Phe Ser Leu Arg Leu Pro Ile Pro Leu Val Lys Thr Pro Pro Ser
1               5                   10                  15

Pro Ser Cys Tyr Tyr Ser His Tyr Tyr His Tyr Arg Tyr Arg Tyr Arg
            20                  25                  30

Cys Tyr His Pro Phe His His Arg Ser Gln Thr Gln Ser Leu Ile Val
        35                  40                  45

Ser Lys Arg Gly Ser Ala Ile Ala Lys Cys His Ala Asp Ser Val Thr
    50                  55                  60

Leu Arg Asp Asp Gly Val Ser Leu Ala Gln Glu Ser Leu Glu Pro Leu
65                  70                  75                  80

Pro Ala Glu Leu Ala Ala Glu Met Met Pro Lys His Val Ala Val Ile
                85                  90                  95

Met Asp Gly Asn Gly Arg Trp Ala Lys Val Lys Gly Leu Pro Pro Ser
            100                 105                 110
```

```
Ala Gly His Gln Ala Gly Val Gln Ser Leu Arg Lys Met Val Arg Leu
            115                 120                 125

Cys Cys Ser Trp Gly Ile Lys Val Leu Thr Val Phe Ala Phe Ser Thr
130                 135                 140

Asp Asn Trp Val Arg Pro Lys Val Glu Val Asp Phe Leu Met Arg Leu
145                 150                 155                 160

Phe Glu Arg Thr Ile Asn Ser Glu Val Gln Thr Phe Lys Arg Glu Gly
                165                 170                 175

Ile Arg Ile Ser Val Ile Gly Asp Ser Ser Arg Leu Pro Glu Ser Leu
            180                 185                 190

Lys Arg Met Ile Ala Ser Ala Glu Glu Asp Thr Lys Gln Asn Ser Arg
            195                 200                 205

Phe Gln Leu Ile Val Ala Val Gly Tyr Ser Gly Lys Tyr Asp Val Val
            210                 215                 220

Gln Ala Cys Lys Ser Val Ala Lys Lys Val Lys Asp Gly His Ile His
225                 230                 235                 240

Leu Asp Asp Ile Asn Glu Asn Ile Ile Glu Gln Glu Leu Glu Thr Asn
                245                 250                 255

Cys Thr Glu Phe Pro Tyr Pro Asp Leu Leu Ile Arg Thr Ser Gly Glu
            260                 265                 270

Leu Arg Val Ser Asn Phe Leu Leu Trp Gln Leu Ala Tyr Thr Glu Leu
            275                 280                 285

Tyr Phe Asn Arg Glu Leu Trp Pro Asp Phe Gly Lys Asp Glu Phe Val
            290                 295                 300

Asp Ala Leu Ser Ser Phe Gln Gln Arg Gln Arg Arg Tyr Gly Gly Arg
305                 310                 315                 320

His Ser

<210> SEQ ID NO 15
<211> LENGTH: 266
<212> TYPE: PRT
<213> ORGANISM: Triticum aestivum

<400> SEQUENCE: 15

Met Pro Leu Ser Asn Ser Thr Ser Ser Val Pro Ala Val Thr Val Pro
1               5                   10                  15

Ala Ala Glu Glu Leu Leu Ser Gln Gly Leu Arg Ala Glu Ser Leu Pro
            20                  25                  30

Arg His Val Ala Leu Val Met Asp Gly Asn Ser Arg Trp Ala Ala Ala
            35                  40                  45

Arg Gly Leu Pro Pro Thr Asp Gly His Glu His Gly Met Arg Ala Leu
50                  55                  60

Met Arg Thr Val Arg Leu Ser Arg Ala Trp Gly Ile Arg Val Leu Thr
65                  70                  75                  80

Ala Phe Gly Phe Ser Leu Glu Asn Trp Asn Arg Pro Lys Ala Glu Val
                85                  90                  95

Asp Phe Leu Met Ala Leu Ile Glu Arg Phe Ile Asn Asp Asn Leu Ala
            100                 105                 110

Glu Phe Leu Arg Glu Gly Thr Arg Leu Arg Ile Ile Gly Asp Arg Ser
            115                 120                 125

Arg Leu Pro Ile Ser Val Gln Lys Thr Ala Arg Asp Ala Glu Glu Ala
            130                 135                 140

Thr Arg Asn Asn Ser Gln Leu Asp Leu Val Leu Ala Ile Ser Tyr Ser
145                 150                 155                 160
```

-continued

```
Gly Arg Met Asp Ile Val Gln Ala Cys Arg Asn Leu Ala Gln Lys Val
                165                 170                 175

Asp Ala Lys Leu Leu Arg Pro Glu Asp Ile Asp Glu Ser Leu Phe Ala
            180                 185                 190

Asp Glu Leu Gln Thr Ser Glu Thr Ser Cys Pro Asp Leu Leu Ile Arg
        195                 200                 205

Thr Ser Gly Glu Leu Arg Leu Ser Asn Phe Leu Leu Trp Gln Ser Ala
    210                 215                 220

Tyr Ser Glu Leu Phe Phe Thr Asp Thr Leu Trp Pro Asp Phe Gly Glu
225                 230                 235                 240

Ala Gln Tyr Leu Gln Ala Met Met Ala Phe Gln Ser Arg Asp Arg Arg
                245                 250                 255

Phe Gly Arg Arg Lys Asn Asn Ala Ala Leu
            260                 265

<210> SEQ ID NO 16
<211> LENGTH: 287
<212> TYPE: PRT
<213> ORGANISM: Dimorphotheca sinuata

<400> SEQUENCE: 16

Met Leu Asn Leu Pro Leu Tyr Leu Pro Lys Tyr Pro Cys Tyr Phe Pro
1               5                   10                  15

Ala Ser Leu Ser Thr Asn His His Arg Gly Leu Tyr Val Phe Asn Gln
            20                  25                  30

Ser Asp Thr Thr Gly Gly Ile Asn Ser Leu Glu Glu Arg Ile Thr
        35                  40                  45

Pro Ala Gly Leu Lys His Glu Leu Met Pro Lys His Val Ala Val Ile
    50                  55                  60

Met Asp Gly Asn Arg Arg Trp Ala Arg Ser Arg Gly Leu Met Pro Asp
65                  70                  75                  80

Ala Gly Tyr Met Glu Gly Ala Arg Ser Leu Lys Val Met Val Glu Leu
                85                  90                  95

Cys Arg Lys Trp Gly Ile Gln Val Leu Thr Val Phe Ala Phe Ser Ala
            100                 105                 110

Asp Asn Trp Leu Arg Pro Lys Val Glu Val Asp Phe Leu Met Gly Leu
        115                 120                 125

Ile Glu Ser Val Leu Lys Asp Glu Val Val His Met Ile Lys Glu Gly
    130                 135                 140

Ile Gln Leu Ser Val Ile Gly Asp Thr Ser Lys Leu Pro Lys Ser Val
145                 150                 155                 160

Lys Arg Ile Ile Thr Tyr Ala Glu Asn Ile Thr Lys Asn Asn Ser Gln
                165                 170                 175

Leu Asn Leu Val Val Ala Ile Asn Tyr Ser Gly Lys Tyr Asp Ile Val
            180                 185                 190

Gln Ala Cys Gln Ser Ile Ala Leu Lys Val Lys Asp Gly Val Ile Gln
        195                 200                 205

Pro Glu Glu Ile Asn Glu Phe Thr Ile Glu Asn Glu Leu Gly Thr Asn
    210                 215                 220

Cys Ile Pro Phe Pro His Pro Asp Leu Leu Ile Arg Thr Ser Gly Glu
225                 230                 235                 240

Leu Arg Val Ser Asn Phe Phe Leu Trp Gln Leu Ala Tyr Thr Glu Leu
                245                 250                 255

Tyr Phe Ser Glu Thr Leu Trp Pro Asp Phe Gly Glu Asp Glu Leu Leu
```

```
                260             265             270
His Ala Leu Asn Thr Phe Gln His Arg Arg Arg Tyr Gly Gly
            275             280             285
```

<210> SEQ ID NO 17
<211> LENGTH: 750
<212> TYPE: DNA
<213> ORGANISM: Micrococcus luteus
<300> PUBLICATION INFORMATION:
<301> AUTHORS: Shimizu,N., Koyama,T. and Ogura,K.
<302> TITLE: Molecular Cloning, Expression, and Purification of
      Undecprenyl Diphosphate Synthase:  No Sequence Similarity
      between E- and Z-prenyl Diphosphate Synthases
<303> JOURNAL: J. Biol. Chem.
<304> VOLUME: 273
<305> ISSUE: 31
<306> PAGES: 19476-19481
<307> DATE: 1998-07-31
<308> DATABASE ACCESSION NUMBER: AB004319
<309> DATABASE ENTRY DATE: 1997-05-29

<400> SEQUENCE: 17

```
atgtttccaa ttaagaagcg aaaagcaata aaaataata acattaatgc ggcacaaatt      60
ccgaaacata ttgcaatcat tatggacgga atggccgat gggcaaaaca gaaaaaaatg     120
ccgcgcataa aaggacatta tgaaggcatg cagaccgtaa agaaaatcac aagatatgct     180
agtgatttag gtgtaaagta cttaacgctg tacgcatttt caactgaaaa ttggtctcgt     240
cctaaagatg aggttaatta cttgatgaaa ctaccgggtg attttttaaa cacattttta     300
ccggaactca ttgaaaaaaa tgttaaagtt gaaacgattg ctttattga tgatttaccg     360
gaccatacaa aaaagcagt gttagaagcg aaagagaaaa cgaaacataa tacaggttta     420
acgctcgtgt ttgcactgaa ttatggtggg cgtaaagaaa ttatttcagc agtgcagtta     480
atcgcagagc gttacaaatc tggtgaaatt tctttagatg aaattagtga aactcatttt     540
aatgaatatt tatttacagc aaatatgcct gatcctgagt tgttaatcag aacttccggt     600
gaagaacgtt taagtaactt tttaatttgg caatgttcat atagtgagtt tgtatttata     660
gatgaattct ggccggattt taatgaagaa agtttagcac aatgtatatc aatatatcag     720
aatcgtcatc gacgttttgg tggattataa                                      750
```

<210> SEQ ID NO 18
<211> LENGTH: 249
<212> TYPE: PRT
<213> ORGANISM: Micrococcus luteus

<400> SEQUENCE: 18

```
Met Phe Pro Ile Lys Lys Arg Lys Ala Ile Lys Asn Asn Ile Asn
1               5                   10                  15

Ala Ala Gln Ile Pro Lys His Ile Ala Ile Ile Met Asp Gly Asn Gly
            20                  25                  30

Arg Trp Ala Lys Gln Lys Lys Met Pro Arg Ile Lys Gly His Tyr Glu
        35                  40                  45

Gly Met Gln Thr Val Lys Lys Ile Thr Arg Tyr Ala Ser Asp Leu Gly
    50                  55                  60

Val Lys Tyr Leu Thr Leu Tyr Ala Phe Ser Thr Glu Asn Trp Ser Arg
65                  70                  75                  80

Pro Lys Asp Glu Val Asn Tyr Leu Met Lys Leu Pro Gly Asp Phe Leu
                85                  90                  95

Asn Thr Phe Leu Pro Glu Leu Ile Glu Lys Asn Val Lys Val Glu Thr
```

```
                100                 105                 110
Ile Gly Phe Ile Asp Asp Leu Pro Asp His Thr Lys Lys Ala Val Leu
        115                 120                 125

Glu Ala Lys Glu Lys Thr Lys His Asn Thr Gly Leu Thr Leu Val Phe
130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Glu Arg Leu Ser Asn Phe Leu
        195                 200                 205

Ile Trp Gln Cys Ser Tyr Ser Glu Phe Val Phe Ile Asp Glu Phe Trp
210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                245
```

<210> SEQ ID NO 19
<211> LENGTH: 861
<212> TYPE: DNA
<213> ORGANISM: Saccharomyces cerevisiae

<400> SEQUENCE: 19

```
atggaaacgg atagtggtat acctggtcat tcatttgtgt taaagtggac aaaaaacatc      60
ttttcgcgca cattgcgtgc atctaactgt gtacctagac atgttgggtt catcatggat     120
gggaacagga gattcgctag aaagaaagag atggacgtaa aggagggcca cgaggcagga     180
tttgttagta tgagtagaat cttagaactg tgttatgaag caggagtcga tacggctacc     240
gtgtttgcct tttcaattga aaatttcaag aggagctcac gggaagttga atcactgatg     300
actttagcgc gcgaaaggat acgacaaatc acagaacgtg gagagctggc ctgtaagtat     360
ggggtacgca ttaaaattat cggcgatctc tctttgttgg ataagtctct attagaagat     420
gttcgggttg ctgtggaaac tacaaagaac aacaaagggc cacgttaaa tatctgcttt      480
ccatatacag gcagggaaga atcttgcat gccatgaaag aaacaattgt tcaacataag      540
aagggcgccg ctatagacga aagcacgtta gaatcgcatc tctacacggc ggggtaccc      600
cctttagatt tattgattag acaagtggc gtttccagat taagtgactt tttgatatgg     660
caggcatcga gtaagggcgt acgcatcgaa ttgctggatt gtttatggcc agagtttgga     720
cctatacgga tggcatggat tttattaaaa ttttcgtttc acaaatcctt tttaaacaaa     780
gagtacagat tagaggaagg tgattatgac gaggaaacca atgggaccc catcgatttg      840
aaagaaaaaa agttgaatta a                                             861
```

<210> SEQ ID NO 20
<211> LENGTH: 286
<212> TYPE: PRT
<213> ORGANISM: Saccharomyces cerevisiae

<400> SEQUENCE: 20

```
Met Glu Thr Asp Ser Gly Ile Pro Gly His Ser Phe Val Leu Lys Trp
1               5                   10                  15

Thr Lys Asn Ile Phe Ser Arg Thr Leu Arg Ala Ser Asn Cys Val Pro
```

|   |   | 20 |   |   |   | 25 |   |   |   | 30 |   |
|---|---|---|---|---|---|---|---|---|---|---|---|

Arg His Val Gly Phe Ile Met Asp Gly Asn Arg Phe Ala Arg Lys
    35                  40                  45

Lys Glu Met Asp Val Lys Glu Gly His Glu Ala Gly Phe Val Ser Met
50                  55                  60

Ser Arg Ile Leu Glu Leu Cys Tyr Glu Ala Gly Val Asp Thr Ala Thr
65                  70                  75                  80

Val Phe Ala Phe Ser Ile Glu Asn Phe Lys Arg Ser Arg Glu Val
            85                  90                  95

Glu Ser Leu Met Thr Leu Ala Arg Glu Arg Ile Arg Gln Ile Thr Glu
        100                  105               110

Arg Gly Glu Leu Ala Cys Lys Tyr Gly Val Arg Ile Lys Ile Ile Gly
        115                  120               125

Asp Leu Ser Leu Leu Asp Lys Ser Leu Leu Glu Asp Val Arg Val Ala
    130                  135               140

Val Glu Thr Thr Lys Asn Asn Lys Arg Ala Thr Leu Asn Ile Cys Phe
145                  150                  155               160

Pro Tyr Thr Gly Arg Glu Glu Ile Leu His Ala Met Lys Glu Thr Ile
        165                  170               175

Val Gln His Lys Lys Gly Ala Ala Ile Asp Glu Ser Thr Leu Glu Ser
        180                  185               190

His Leu Tyr Thr Ala Gly Val Pro Pro Leu Asp Leu Leu Ile Arg Thr
    195                  200               205

Ser Gly Val Ser Arg Leu Ser Asp Phe Leu Ile Trp Gln Ala Ser Ser
    210                  215               220

Lys Gly Val Arg Ile Glu Leu Leu Asp Cys Leu Trp Pro Glu Phe Gly
225                  230                  235               240

Pro Ile Arg Met Ala Trp Ile Leu Leu Lys Phe Ser Phe His Lys Ser
        245                  250               255

Phe Leu Asn Lys Glu Tyr Arg Leu Glu Glu Gly Asp Tyr Asp Glu Glu
        260                  265               270

Thr Asn Gly Asp Pro Ile Asp Leu Lys Glu Lys Lys Leu Asn
    275                  280               285

<210> SEQ ID NO 21
<211> LENGTH: 1032
<212> TYPE: DNA
<213> ORGANISM: Saccharomyces cerevisiae

<400> SEQUENCE: 21

```
atgaaaatgc ccagtattat tcagattcag tttgtagccc taaaaaggct tttggtagaa      60
accaaagaac agatgtgctt cgcagtgaaa agtatatttc agagagtatt tgcgtgggtt     120
atgtcattaa gcttgttttc atggttttat gtaaatcttc agaatatttt gataaaagca     180
ttaagggtag ggccagtgcc tgaacatgtc cctttatca tggatggtaa ccggagatat      240
gccaagtcaa gaaggctacc agtaaaaaaa ggccatgaag ctggtgggtt aacgttacta     300
acactactgt atatctgcaa agattgggt gtaaatgtg tttccgccta tgcattttct       360
attgaaaatt ttaatagacc aaaagaagaa gtagatacgc taatgaattt gtttacggta     420
aagcttgatg aattcgcaaa aagagccaag gactataagg atccctata cggatctaaa      480
ataagaatag taggtgatca atctttacta tctccagaaa tgagaaaaaa aattaaaaaa     540
gtggaagaaa tcacacagga tggagacgat tcactttat ttatatgttt tccttacact      600
tcaagaaatg atatgttaca tactattcgt gattcagttg aagaccattt ggaaaataaa     660
```

-continued

```
tcaccaagga ttaatataag aaaatttact aataaaatgt acatgggttt ccattccaat    720
aaatgtgaat tattaatcag aacaagtggg cataggaggc tctcagacta tgctatgg     780 caagtacatg aaaatgccac cattgaattt agtgatacgt tgtggccaaa ttttagcttc    840
tttgctatgt acctgatgat tctcaaatgg tccttctttt ccaccattca aaatataat    900 gagaagaatc actcattgtt tgaaaaaata catgaaagcg ttccttcaat atttaaaaaa   960
aagaaaacag ctatgtcttt gtacaacttt ccaaaccccc ccatttcagt ttcggttaca   1020
ggagatgaat aa                                                       1032
```

<210> SEQ ID NO 22
<211> LENGTH: 343
<212> TYPE: PRT
<213> ORGANISM: Saccharomyces cerevisiae

<400> SEQUENCE: 22

```
Met Lys Met Pro Ser Ile Ile Gln Ile Gln Phe Val Ala Leu Lys Arg
1               5                   10                  15

Leu Leu Val Glu Thr Lys Glu Gln Met Cys Phe Ala Val Lys Ser Ile
                20                  25                  30

Phe Gln Arg Val Phe Ala Trp Val Met Ser Leu Ser Leu Phe Ser Trp
            35                  40                  45

Phe Tyr Val Asn Leu Gln Asn Ile Leu Ile Lys Ala Leu Arg Val Gly
        50                  55                  60

Pro Val Pro Glu His Val Ser Phe Ile Met Asp Gly Asn Arg Arg Tyr
65                  70                  75                  80

Ala Lys Ser Arg Arg Leu Pro Val Lys Lys Gly His Glu Ala Gly Gly
                85                  90                  95

Leu Thr Leu Leu Thr Leu Leu Tyr Ile Cys Lys Arg Leu Gly Val Lys
            100                 105                 110

Cys Val Ser Ala Tyr Ala Phe Ser Ile Glu Asn Phe Asn Arg Pro Lys
        115                 120                 125

Glu Glu Val Asp Thr Leu Met Asn Leu Phe Thr Val Lys Leu Asp Glu
130                 135                 140

Phe Ala Lys Arg Ala Lys Asp Tyr Lys Asp Pro Leu Tyr Gly Ser Lys
145                 150                 155                 160

Ile Arg Ile Val Gly Asp Gln Ser Leu Leu Ser Pro Glu Met Arg Lys
                165                 170                 175

Lys Ile Lys Lys Val Glu Glu Ile Thr Gln Asp Gly Asp Asp Phe Thr
            180                 185                 190

Leu Phe Ile Cys Phe Pro Tyr Thr Ser Arg Asn Asp Met Leu His Thr
        195                 200                 205

Ile Arg Asp Ser Val Glu Asp His Leu Glu Asn Lys Ser Pro Arg Ile
210                 215                 220

Asn Ile Arg Lys Phe Thr Asn Lys Met Tyr Met Gly Phe His Ser Asn
225                 230                 235                 240

Lys Cys Glu Leu Leu Ile Arg Thr Ser Gly His Arg Arg Leu Ser Asp
                245                 250                 255

Tyr Met Leu Trp Gln Val His Glu Asn Ala Thr Ile Glu Phe Ser Asp
            260                 265                 270

Thr Leu Trp Pro Asn Phe Ser Phe Ala Met Tyr Leu Met Ile Leu
        275                 280                 285

Lys Trp Ser Phe Phe Ser Thr Ile Gln Lys Tyr Asn Glu Lys Asn His
290                 295                 300
```

```
Ser Leu Phe Glu Lys Ile His Glu Ser Val Pro Ser Ile Phe Lys Lys
305                 310                 315                 320

Lys Lys Thr Ala Met Ser Leu Tyr Asn Phe Pro Asn Pro Pro Ile Ser
            325                 330                 335

Val Ser Val Thr Gly Asp Glu
            340

<210> SEQ ID NO 23
<211> LENGTH: 271
<212> TYPE: PRT
<213> ORGANISM: Arabidopsis

<400> SEQUENCE: 23

Met Asn Thr Leu Glu Glu Val Asp Glu Ser Thr His Ile Phe Asn Ala
1               5                   10                  15

Leu Met Ser Leu Met Arg Lys Phe Leu Phe Arg Val Leu Cys Val Gly
            20                  25                  30

Pro Ile Pro Thr Asn Ile Ser Phe Ile Met Asp Gly Asn Arg Arg Phe
        35                  40                  45

Ala Lys Lys His Asn Leu Ile Gly Leu Asp Ala Gly His Arg Ala Gly
    50                  55                  60

Phe Ile Ser Val Lys Tyr Ile Leu Gln Tyr Cys Lys Glu Ile Gly Val
65                  70                  75                  80

Pro Tyr Val Thr Leu His Ala Phe Gly Met Asp Asn Phe Lys Arg Gly
                85                  90                  95

Pro Glu Glu Val Lys Cys Val Met Asp Leu Met Leu Glu Lys Val Glu
            100                 105                 110

Leu Ala Ile Asp Gln Ala Val Ser Gly Asn Met Asn Gly Val Arg Ile
        115                 120                 125

Ile Phe Ala Gly Asp Leu Asp Ser Leu Asn Glu His Phe Arg Ala Ala
    130                 135                 140

Thr Lys Lys Leu Met Glu Leu Thr Glu Glu Asn Arg Asp Leu Ile Val
145                 150                 155                 160

Val Val Cys Val Ala Tyr Ser Thr Ser Leu Glu Ile Val His Ala Val
                165                 170                 175

Arg Lys Ser Cys Val Arg Lys Cys Thr Asn Gly Asp Asp Leu Val Leu
            180                 185                 190

Leu Glu Leu Ser Asp Val Glu Glu Cys Met Tyr Thr Ser Ile Val Pro
        195                 200                 205

Val Pro Asp Leu Val Ile Arg Thr Gly Gly Gly Asp Arg Leu Ser Asn
    210                 215                 220

Phe Met Thr Trp Gln Thr Ser Arg Ser Leu Leu His Arg Thr Glu Ala
225                 230                 235                 240

Leu Trp Pro Glu Leu Gly Leu Trp His Leu Val Trp Ala Ile Leu Lys
                245                 250                 255

Phe Gln Arg Met Gln Asp Tyr Leu Thr Lys Lys Lys Leu Asp
            260                 265                 270

<210> SEQ ID NO 24
<211> LENGTH: 295
<212> TYPE: PRT
<213> ORGANISM: Arabidopsis

<400> SEQUENCE: 24

Met Ala Glu Leu Pro Gly Gln Ile Arg His Ile Gly Gly Arg Met Ser
1               5                   10                  15
```

```
Gln Leu Leu Glu Gln Ile Tyr Gly Phe Ser Arg Arg Ser Leu Phe Arg
             20                  25                  30

Val Ile Ser Met Gly Pro Ile Pro Cys His Ile Ala Phe Ile Met Asp
         35                  40                  45

Gly Asn Arg Arg Tyr Ala Lys Lys Cys Gly Leu Leu Asp Gly Ser Gly
     50                  55                  60

His Lys Ala Gly Phe Ser Ala Leu Met Ser Met Leu Gln Tyr Cys Tyr
 65                  70                  75                  80

Glu Leu Gly Ile Lys Tyr Val Thr Ile Tyr Ala Phe Ser Ile Asp Asn
                 85                  90                  95

Phe Arg Arg Lys Pro Glu Glu Val Glu Ser Val Met Asp Leu Met Leu
             100                 105                 110

Glu Lys Ile Lys Ser Leu Leu Glu Lys Glu Ser Ile Val His Gln Tyr
         115                 120                 125

Gly Ile Arg Val Tyr Phe Ile Gly Asn Leu Ala Leu Leu Asn Asp Gln
     130                 135                 140

Val Arg Ala Ala Ala Glu Lys Val Met Lys Ala Thr Ala Lys Asn Ser
145                 150                 155                 160

Arg Val Val Leu Leu Ile Cys Ile Ala Tyr Asn Ser Thr Asp Glu Ile
                 165                 170                 175

Val Gln Ala Val Lys Lys Ser Cys Ile Asn Lys Ser Asp Asn Ile Glu
             180                 185                 190

Ala Ser Asn Tyr Lys His Glu Asp Ser Asp Ser Asp Ile Glu Gly Thr
         195                 200                 205

Asp Met Glu Asn Gln Glu Lys Lys Ile Gln Leu Val Asp Ile Glu Glu
     210                 215                 220

Asn Met Gln Met Ser Val Ala Pro Asn Pro Asp Ile Leu Ile Arg Ser
225                 230                 235                 240

Ser Gly Glu Thr Arg Leu Ser Asn Phe Leu Leu Trp Gln Thr Gly Asn
                 245                 250                 255

Thr Gln Leu Cys Ser Pro Ala Ala Leu Trp Pro Glu Ile Gly Leu Arg
             260                 265                 270

His Leu Leu Trp Ala Ile Leu Asn Phe Gln Arg Asn His Ser Tyr Leu
         275                 280                 285

Glu Lys Arg Lys Lys Gln Leu
     290                 295

<210> SEQ ID NO 25
<211> LENGTH: 303
<212> TYPE: PRT
<213> ORGANISM: Arabidopsis

<400> SEQUENCE: 25

Met Leu Ser Leu Leu Ser Ser Asp Ser Ser Leu Leu Ser Leu Leu Phe
 1               5                  10                  15

Leu Phe Leu Ile Pro Cys Leu Phe Ile Thr Ser Tyr Ile Gly Phe Pro
             20                  25                  30

Val Phe Leu Leu Lys Leu Ile Gly Leu Ile Lys Ile Lys Ala Ala Arg
         35                  40                  45

Asp Asn Glu Lys Arg Asp Glu Gly Thr Tyr Val Val Arg Glu Asp Gly
     50                  55                  60

Leu Gln Arg Glu Leu Met Pro Arg His Val Ala Phe Ile Leu Asp Gly
 65                  70                  75                  80

Asn Arg Arg Trp Ala Lys Arg Ala Gly Leu Thr Thr Ser Gln Gly His
```

```
                     85                  90                  95
Glu Ala Gly Ala Lys Arg Leu Ile Asp Ile Ala Glu Leu Cys Phe Glu
                100                 105                 110
Leu Gly Val His Thr Val Ser Ala Phe Ala Phe Ser Thr Glu Asn Trp
            115                 120                 125
Gly Arg Asp Lys Ile Glu Ile Asp Asn Leu Met Ser Leu Ile Gln His
        130                 135                 140
Tyr Arg Asn Lys Ser Asn Ile Lys Phe Phe His Arg Ser Glu Val Arg
145                 150                 155                 160
Val Ser Val Ile Gly Asn Lys Thr Lys Ile Pro Glu Ser Leu Leu Lys
                165                 170                 175
Glu Ile His Glu Ile Glu Glu Ala Thr Lys Gly Tyr Lys Asn Lys His
                180                 185                 190
Leu Ile Met Ala Val Asp Tyr Ser Gly Lys Phe Asp Ile Met His Ala
            195                 200                 205
Cys Lys Ser Leu Val Lys Lys Ser Glu Lys Gly Leu Ile Arg Glu Glu
        210                 215                 220
Asp Val Asp Glu Ala Leu Ile Glu Arg Glu Leu Leu Thr Asn Cys Ser
225                 230                 235                 240
Asp Phe Pro Ser Pro Asp Leu Met Ile Arg Thr Ser Gly Glu Gln Arg
                245                 250                 255
Ile Ser Asn Phe Phe Leu Trp Gln Leu Ala Tyr Ser Glu Leu Phe Phe
                260                 265                 270
Ser Pro Val Phe Trp Pro Asp Phe Asp Lys Asp Lys Leu Leu Glu Ala
            275                 280                 285
Leu Ala Ser Tyr Gln Arg Arg Glu Arg Arg Phe Gly Cys Arg Val
        290                 295                 300

<210> SEQ ID NO 26
<211> LENGTH: 244
<212> TYPE: PRT
<213> ORGANISM: Arabidopsis

<400> SEQUENCE: 26

Met Gly Glu Lys Gln Lys Arg Gly Arg Asn Ile Met Pro Lys His Val
1                   5                   10                  15
Ala Val Ile Leu Asp Gly Asn Arg Arg Trp Ala Glu Lys Arg Gly Leu
                20                  25                  30
Gly Thr Ser Glu Gly His Glu Ala Gly Ala Arg Arg Leu Met Glu Asn
            35                  40                  45
Ala Lys Asp Cys Phe Ala Met Gly Thr Asn Thr Ile Ser Leu Phe Ala
        50                  55                  60
Phe Ser Thr Glu Asn Trp Glu Arg Pro Glu Asp Val Lys Cys Leu
65                  70                  75                  80
Met Ala Leu Phe Glu Lys Tyr Leu Ala Ser Asp Met Pro Tyr Leu Arg
                85                  90                  95
Ser Asp Lys Ile Lys Ile Ser Val Ile Gly Asn Arg Thr Lys Leu Pro
                100                 105                 110
Glu Ser Leu Leu Gly Leu Ile Glu Glu Val Glu Glu Ala Thr Lys Ser
            115                 120                 125
Tyr Glu Gly Lys Asn Leu Ile Ile Ala Ile Asp Tyr Ser Gly Arg Tyr
        130                 135                 140
Asp Ile Leu Gln Ala Cys Lys Ser Leu Ala Asn Lys Val Lys Asp Gly
145                 150                 155                 160
```

```
Leu Ile Gln Val Glu Asp Ile Asn Glu Lys Ala Met Glu Lys Glu Leu
                165                 170                 175

Leu Thr Lys Cys Ser Glu Phe Pro Asn Pro Asp Leu Leu Ile Arg Thr
            180                 185                 190

Ser Gly Glu Gln Arg Ile Ser Asn Phe Phe Leu Trp Gln Ser Ala Tyr
        195                 200                 205

Thr Glu Leu Tyr Phe Pro Thr Val Leu Trp Pro Asp Phe Gly Glu Ala
    210                 215                 220

Glu Tyr Leu Glu Ala Leu Thr Trp Tyr Gln Gln Arg Gln Arg Arg Phe
225                 230                 235                 240

Gly Arg Arg Val

<210> SEQ ID NO 27
<211> LENGTH: 21
<212> TYPE: PRT
<213> ORGANISM: Artificial Sequence
<220> FEATURE:
<223> OTHER INFORMATION: Domain IV consensus sequence from Figure 1
      alignment
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid
<220> FEATURE:
<221> NAME/KEY: MISC_FEATURE
<222> LOCATION: (16)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid

<400> SEQUENCE: 27

Tyr Ser Gly Arg Xaa Glu Ile Val Xaa Ala Val Lys Xaa Ser Xaa Xaa
1               5                   10                  15

Lys Xaa Xaa Xaa Gly
            20

<210> SEQ ID NO 28
<211> LENGTH: 47
<212> TYPE: PRT
<213> ORGANISM: Artificial Sequence
<220> FEATURE:
<223> OTHER INFORMATION: Domain V consensus sequence from Figure 1
      alignment
<220> FEATURE:
<221> NAME/KEY: MISC_FEATURE
<222> LOCATION: (2)..(2)
<223> OTHER INFORMATION: Xaa = any amino acid
<220> FEATURE:
```

```
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = any amino acid
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid
<220> FEATURE:
<221> NAME/KEY: MISC_FEATURE
<222> LOCATION: (16)..(16)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = any amino acid
<220> FEATURE:
<221> NAME/KEY: MISC_FEATURE
<222> LOCATION: (35)..(35)
<223> OTHER INFORMATION: Xaa = any amino acid

<400> SEQUENCE: 28

Ile Xaa Xaa Xaa Glu Ile Xaa Xaa Xaa Leu Xaa Asp Xaa Glu Leu Xaa
1               5                   10                  15

Xaa Asn Xaa Xaa Xaa Xaa Pro Xaa Pro Asp Leu Leu Ile Arg Thr Ser
            20                  25                  30

Gly Glu Xaa Arg Leu Ser Asn Phe Leu Leu Trp Gln Thr Ala Tyr
        35                  40                  45

<210> SEQ ID NO 29
<211> LENGTH: 13
<212> TYPE: PRT
<213> ORGANISM: Artificial Sequence
<220> FEATURE:
<223> OTHER INFORMATION: Consensus Sequence from Apfel CM et al. (J
      Bacteriol 1999 Jan;181 (2):483-492)
```

```
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = W or Y or F
<220> FEATURE:
<221> NAME/KEY: MISC_FEATURE
<222> LOCATION: (10)..(10)
<223> OTHER INFORMATION: Xaa = R or G

<400> SEQUENCE: 29

His Xaa Xaa Xaa Xaa Met Asp Gly Asn Xaa Arg Xaa Ala
1               5                   10

<210> SEQ ID NO 30
<211> LENGTH: 5
<212> TYPE: PRT
<213> ORGANISM: Artificial Sequence
<220> FEATURE:
<223> OTHER INFORMATION: Consensus Sequence  from Apfel CM et al. (J
      Bacteriol 1999 Jan;18 1(2):483-492)
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 30

Gly His Xaa Xaa Gly
1               5

<210> SEQ ID NO 31
<211> LENGTH: 23
<212> TYPE: PRT
<213> ORGANISM: Artificial Sequence
<220> FEATURE:
<223> OTHER INFORMATION: Consensus Sequence from Apfel CM et al. (J
      Bacteriol 1999 Jan;181 (2):483-492)
<220> FEATURE:
<221> NAME/KEY: MISC_FEATURE
<222> LOCATION: (1)..(1)
<223> OTHER INFORMATION: Xaa = T or S
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = S or T
<220> FEATURE:
<221> NAME/KEY: MISC_FEATURE
<222> LOCATION: (10)..(10)
```

```
<223> OTHER INFORMATION: Xaa = any amino acid
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid
<220> FEATURE:
<221> NAME/KEY: MISC_FEATURE
<222> LOCATION: (14)..(14)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid

<400> SEQUENCE: 31

Xaa Xaa Xaa Ala Phe Ser Xaa Glu Asn Xaa Xaa Arg Xaa Xaa Xaa Glu
1               5                   10                  15

Val Xaa Xaa Leu Met Xaa Leu
            20

<210> SEQ ID NO 32
<211> LENGTH: 13
<212> TYPE: PRT
<213> ORGANISM: Artificial Sequence
<220> FEATURE:
<223> OTHER INFORMATION: Consensus Sequence from Apfel CM et al. (J
      Bacteriol 1999 Jan;181 (2):483-492)
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = D or E
<220> FEATURE:
<221> NAME/KEY: MISC_FEATURE
<222> LOCATION: (10)..(10)
<223> OTHER INFORMATION: Xaa =   L or I or V or M
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = any amino acid

<400> SEQUENCE: 32

Ala Xaa Xaa Tyr Gly Gly Arg Xaa Xaa Xaa Xaa Xaa Ala
1               5                   10
```

```
<210> SEQ ID NO 33
<211> LENGTH: 35
<212> TYPE: PRT
<213> ORGANISM: Artificial Sequence
<220> FEATURE:
<223> OTHER INFORMATION: Consensus Sequence from Apfel CM et al. (J
      Bacteriol 1999 Jan;181 (2):483-492)
<220> FEATURE:
<221> NAME/KEY: MISC_FEATURE
<222> LOCATION: (1)..(1)
<223> OTHER INFORMATION: Xaa = D or E
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = S or A or G
<220> FEATURE:
<221> NAME/KEY: MISC_FEATURE
<222> LOCATION: (10)..(10)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = any amino acid
<220> FEATURE:
<221> NAME/KEY: MISC_FEATURE
<222> LOCATION: (16)..(16)
<223> OTHER INFORMATION: Xaa = M or L
<220> FEATURE:
<221> NAME/KEY: MISC_FEATURE
<222> LOCATION: (17)..(17)
<223> OTHER INFORMATION: Xaa = L or M or P
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = S or A or T
<220> FEATURE:
<221> NAME/KEY: MISC_FEATURE
<222> LOCATION: (25)..(25)
<223> OTHER INFORMATION: Xaa = any amino acid
<220> FEATURE:
<221> NAME/KEY: MISC_FEATURE
<222> LOCATION: (26)..(26)
<223> OTHER INFORMATION: Xaa = any amino acid
<220> FEATURE:
<221> NAME/KEY: MISC_FEATURE
<222> LOCATION: (28)..(28)
<223> OTHER INFORMATION: Xaa = any amino acid
<220> FEATURE:
<221> NAME/KEY: MISC_FEATURE
<222> LOCATION: (29)..(29)
<223> OTHER INFORMATION: Xaa = any amino acid
<220> FEATURE:
<221> NAME/KEY: MISC_FEATURE
<222> LOCATION: (30)..(30)
<223> OTHER INFORMATION: Xaa = any amino acid
<220> FEATURE:
<221> NAME/KEY: MISC_FEATURE
<222> LOCATION: (31)..(31)
<223> OTHER INFORMATION: Xaa = any amino acid
<220> FEATURE:
<221> NAME/KEY: MISC_FEATURE
<222> LOCATION: (34)..(34)
<223> OTHER INFORMATION: Xaa = D or E

<400> SEQUENCE: 33
```

```
Xaa Leu Xaa Ile Arg Thr Xaa Gly Glu Xaa Arg Xaa Ser Asn Phe Xaa
1               5                   10                  15

Xaa Trp Gln Xaa Xaa Tyr Xaa Glu Xaa Xaa Phe Xaa Xaa Xaa Xaa Trp
            20                  25                  30

Pro Xaa Phe
        35

<210> SEQ ID NO 34
<211> LENGTH: 35
<212> TYPE: PRT
<213> ORGANISM: Artificial Sequence
<220> FEATURE:
<223> OTHER INFORMATION: Consensus Sequence

<400> SEQUENCE: 34

Asp Ile Leu Val Arg Ser Ser Gly Glu Thr Arg Leu Ser Asn Phe Leu
1               5                   10                  15

Leu Trp Gln Thr Thr Asn Cys Val Leu Tyr Ser Pro Lys Ala Leu Trp
            20                  25                  30

Pro Glu Met
        35

<210> SEQ ID NO 35
<211> LENGTH: 10
<212> TYPE: PRT
<213> ORGANISM: Artificial Sequence
<220> FEATURE:
<223> OTHER INFORMATION: Artificial and non-naturally occurring peptide

<400> SEQUENCE: 35

Glu Leu Val Ile Ser Leu Ile Val Glu Ser
1               5                   10

<210> SEQ ID NO 36
<211> LENGTH: 21
<212> TYPE: DNA
<213> ORGANISM: Artificial Sequence
<220> FEATURE:
<223> OTHER INFORMATION: Primer NKH46

<400> SEQUENCE: 36
ttcgccggag ctccttacta a                                          21

<210> SEQ ID NO 37
<211> LENGTH: 23
<212> TYPE: DNA
<213> ORGANISM: Artificial Sequence
<220> FEATURE:
<223> OTHER INFORMATION: Primer NKH45

<400> SEQUENCE: 37
cgttcatgac ccgtatgctt tct                                        23

<210> SEQ ID NO 38
<211> LENGTH: 11
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (4)..(4)
<223> OTHER INFORMATION: Xaa = L or M

<400> SEQUENCE: 38
```

```
Ala Phe Ile Xaa Asp Gly Asn Arg Arg Phe Ala
1               5                   10
```

<210> SEQ ID NO 39
<211> LENGTH: 10
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (2)..(2)
<223> OTHER INFORMATION: Xaa = T or S
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = D or E
<220> FEATURE:
<221> NAME/KEY: MISC_FEATURE
<222> LOCATION: (8)..(8)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = any amino acid

<400> SEQUENCE: 39

```
Tyr Xaa Ser Xaa Xaa Xaa Ile Xaa Xaa Ala
1               5                   10
```

<210> SEQ ID NO 40
<211> LENGTH: 22
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = I or V
<220> FEATURE:
<221> NAME/KEY: MISC_FEATURE
<222> LOCATION: (7)..(7)
<223> OTHER INFORMATION: Xaa = I or V
<220> FEATURE:
<221> NAME/KEY: MISC_FEATURE
<222> LOCATION: (9)..(9)
<223> OTHER INFORMATION: Xaa = S or T
<220> FEATURE:
<221> NAME/KEY: MISC_FEATURE
<222> LOCATION: (12)..(12)
<223> OTHER INFORMATION: Xaa = E or L
<220> FEATURE:
<221> NAME/KEY: MISC_FEATURE
<222> LOCATION: (13)..(13)
<223> OTHER INFORMATION: Xaa = S or T
<220> FEATURE:
<221> NAME/KEY: MISC_FEATURE
<222> LOCATION: (18)..(18)
<223> OTHER INFORMATION: Xaa = any amino acid

<400> SEQUENCE: 40

```
Pro Xaa Pro Asp Xaa Leu Xaa Arg Xaa Ser Gly Xaa Xaa Arg Leu Ser
1               5                   10                  15

Asn Xaa Leu Leu Trp Gln
            20
```

<210> SEQ ID NO 41
<211> LENGTH: 22
<212> TYPE: DNA
<213> ORGANISM: Artificial Sequence
<220> FEATURE:
<223> OTHER INFORMATION: Primer Dan5

<400> SEQUENCE: 41
ctcgacaatt tcaatcgacg cc                                    22

<210> SEQ ID NO 42
<211> LENGTH: 22
<212> TYPE: DNA
<213> ORGANISM: Artificial Sequence
<220> FEATURE:
<223> OTHER INFORMATION: Primer Dan6

<400> SEQUENCE: 42
gaaggaagtt gctcagccct tgt                                   22

<210> SEQ ID NO 43
<211> LENGTH: 21
<212> TYPE: DNA
<213> ORGANISM: Artificial Sequence
<220> FEATURE:
<223> OTHER INFORMATION: Primer DegHptS

<400> SEQUENCE: 43
atawtggatg gaaacmggag g                                     21

<210> SEQ ID NO 44
<211> LENGTH: 20
<212> TYPE: DNA
<213> ORGANISM: Artificial Sequence
<220> FEATURE:
<223> OTHER INFORMATION: Primer NKH5
<220> FEATURE:
<221> NAME/KEY: misc_feature
<222> LOCATION: (6)..(6)
<223> OTHER INFORMATION: n = Inosine
<220> FEATURE:
<221> NAME/KEY: misc_feature
<222> LOCATION: (8)..(8)
<223> OTHER INFORMATION: n = Inosine

<400> SEQUENCE: 44
tgccananha dgwarttrct                                       20

<210> SEQ ID NO 45
<211> LENGTH: 208
<212> TYPE: PRT
<213> ORGANISM: Taraxacum kok-saghyz

<400> SEQUENCE: 45

```
Leu Val Phe Ile Leu Asp Gly Asn Arg Arg Phe Ala Arg Lys Trp Asn
1               5                   10                  15

Leu Thr Glu Gly Ala Gly His Lys Thr Gly Phe Leu Ala Leu Met Ser
            20                  25                  30

Val Leu Lys Tyr Cys Tyr Glu Ile Gly Val Lys Tyr Val Thr Ile Tyr
        35                  40                  45
```

```
Ala Phe Ser Leu Asp Asn Phe Asn Arg Arg Pro Asp Glu Val Gln Tyr
     50                  55                  60

Val Met Asp Leu Met Gln Asp Lys Ile Glu Gly Phe Leu Lys Glu Val
65                   70                  75                   80

Ser Ile Ile Asn Gln Tyr Gly Val Arg Val Leu Phe Ile Gly Asp Leu
                 85                  90                  95

Asp Arg Leu Tyr Glu Pro Val Arg Ile Ala Ala Glu Lys Ala Met Glu
             100                 105                 110

Ala Thr Ala Lys Asn Ser Thr Thr Tyr Leu Leu Val Cys Val Ala Tyr
             115                 120                 125

Thr Ser Ser His Glu Ile Pro Arg Ala Ile His Glu Ala Cys Glu Glu
         130                 135                 140

Ser Ile Arg Val Met Asn Gly Asn Gly Phe Phe Asn Gly Ser Gly Tyr
145                 150                 155                 160

Thr Asn Val Asn His Gly Ser Gln Ala Val Ile Lys Val Val Asp Leu
                 165                 170                 175

Asp Lys His Met Tyr Met Gly Val Ala Pro Asp Pro Asp Ile Leu Val
             180                 185                 190

Arg Ser Ser Gly Glu Thr Arg Leu Ser Asn Phe Leu Leu Trp His Lys
         195                 200                 205
```

CIS-PRENYLTRANSFERASES FROM THE RUBBER-PRODUCING PLANTS RUSSIAN DANDELION (TARAXACUM KOK-SAGHYZ) AND SUNFLOWER (HELIANTHUS ANNUS)

FIELD OF THE INVENTION

This invention is in the field of plant molecular biology. More specifically, this invention pertains to the identification of cis-prenyltransferase genes preferentially expressed in the rubber-producing plants *Taraxacum kok-saghyz* (russian dandelion) and *Helianthus annus* (sunflower) and their utility in altering natural rubber production in transgenic plants.

BACKGROUND OF THE INVENTION

Natural rubber (cis-1,4-polyisoprene) is produced in about 2000 plant species (usually as a constituent of plant latex) with varying degrees of quality and quantity. Several well-studied examples of rubber-producing plants include:
1. Indian laurel (*Ficus elastica*), a well-known household plant that produces a rubber-containing latex.
2. Trees of the Sapotacae family (*Palaquim gutta* and *P. oblongifolia*), located in the Malaysian peninsula and responsible for gutta percha latex (a viscous, grayish latex that exudes slowly from cuts in the bark and rapidly turns brown after exposure to the air).
3. The tropical American tree *Mimusops balata*, which produces Balata latex as white or reddish exudates.
4. The tropical American saprodilla tree *Archras zapote*, which produces Chicle
5. The Central American tree *Castilla elastica*, which produces caucho negro rubber.
6. The Brazilian species, *Manihot glazovii*, which produces ceara rubber.
7. The dandelion species kok-saghyz (*Taraxacum kok-saghyz*; from Kazakhstan) and krim-saghyz (*T. megalorhizon*; found in the Crimea and throughout the Mediterranean region), which produce a high-quality rubber in their roots.
8. The non-latex producing American desert shrub guayule (*Parthenium argentatum*), in which rubber is produced seasonally within parenchymatous cells of the stem and root, and its isolation requires harvesting of the plant and maceration of the tissue.

The natural rubbers produced by each of these species differ in one or more of their properties. In particular, differences in molecular weight and molecular weight distribution have been observed in natural rubbers depending on their plant origin (Backhaus, R. A. *Israel Journal of Botany* 34: 283–293 (1985)).

Natural rubber, despite the development of many synthetic polymer alternatives, remains a high-volume commodity material based on its superior properties of elasticity, resilience, and resistance to high temperature. Currently, some 6,810,000 tons of natural rubber are produced annually. Despite this abundance, latex tapped from the tree *Hevea brasiliensis* is today the only significant commercial source of natural rubber and it is expected that global demand will soon be greater than supplies. Thus, there is significant interest in studying rubber biosynthesis and the differences between rubber produced by *Hevea* to other natural rubbers, in order to develop alternative rubber-sources. In particular, it would be useful to industry to have available rubbers with different molecular weight averages (higher and lower than Hevea rubber) and distributions. For example, rubbers with molecular weights lower than those obtained from *H. brasiliensis* may have distinct advantages over the Hevea material in certain applications due to their ease of processing (Nor, H. M., and Ebdon, J. R. *Progress in Polymer Sci.* 23: 143–177 (1998); Meeker, T. Low Molecular Weight Polyisoprenes Offer Versatility In Bonding Techniques. Adhesives Age; pp. 23–26 (July 1998)). Although the molecular weights of rubbers synthesized in in vitro experiments with isolated, enzymatically-active rubber particles are highly influenced by the concentrations of initiator allylic diphosphate and isopentenyl diphosphate (IPP), the intrinsic properties of the cis-prenyltransferases themselves also play a role in determining the size of the rubber molecules they produce (Cornish, K. *Phytochemistry* 57: 1123–1134 (2001)).

Cis-prenyltransferases are a family of enzymes that are responsible for synthesizing natural rubbers, by catalyzing the sequential addition of $C_5$ units (in the form of isopentenyl pyrophosphate (IPP)) to an initiator molecule in head-to-tail condensation reactions. The initiator molecules themselves are derived from isoprene units through the action of distinct prenyltransferases. These initiators are allylic terpenoid diphosphates such as dimethylallyldiphosphate (DMAPP; $C_5$), geranyl diphosphate (GPP; $C_{10}$), farnesyl diphosphate (FPP; $C_{15}$), and geranylgeranyl diphosphate (GGPP; $C_{20}$). Genes encoding the enzymes which synthesize these allylic terpenoid diphosphates have been cloned from a number of organisms, including plants, and all of these genes encode polypeptides with conserved regions of homology (McGarvey et al., *Plant Cell* 7:1015–1026 (1995); Chappell, J., *Annu. Rev. Plant Physiol. Plant Mol. Biol.* 46:521–547 (1995)). All of these gene products condense isoprene units in the trans- configuration. Prenyltransferases that condense isoprene units in a cis-configuration have only recently been identified in microbes and plants. Most notable to the present disclosure herein is the discovery of cis-prenyltransferase gene products in latex of the rubber-producing species *Hevea brasiliensis* (WO01/21650; GenBank Accession Numbers AY124934, AY124474, AY124473, AY124472, AY124471, AY124470, AY124469, AY124468, AY124467, AY124466, AY124465, AY124464; see also AB061236 and AB074307).

In the present disclosure, the problem to be solved therefore is to identify new plant cis-prenyltransferase genes. These genes will have utility in modification of the properties of natural rubbers obtained from plants. Applicants have solved the stated problem by identifying plant genes encoding cis-prenyltransferases from rubber-producing russian dandelion and sunflower species (both of which produce natural rubbers with different properties than those obtained from *H. brasiliensis*). Additionally, Applicants have discovered diagnostic features within the gene sequences of cis-prenyltransferases from rubber-producing species.

SUMMARY OF THE INVENTION

Accordingly the invention provides an isolated nucleic acid molecule encoding a cis-prenyltransferase enzyme, selected from the group consisting of:
a) an isolated nucleic acid molecule encoding the amino acid sequence as set forth in SEQ ID NOs:4 and 6;
b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or
an isolated nucleic acid molecule that is complementary to (a) or (b).

Specifically the invention provides an isolated nucleic acid molecule comprising a first nucleotide sequence encoding a polypeptide of at least 301 amino acids that has at least 70% identity based on the Smith-Waterman method of alignment when compared to a polypeptide having the sequence as set forth in SEQ ID NO:4 or a second nucleotide sequence comprising the complement of the first nucleotide sequence, wherein said enzyme has cis-prenyltransferase activity.

In similar fashion the invention provides An isolated nucleic acid molecule comprising a first nucleotide sequence encoding a polypeptide of at least 168 amino acids that has at least 70% identity based on the Smith-Waterman method of alignment when compared to a polypeptide having the sequence as set forth in SEQ ID NO:6 or a second nucleotide sequence comprising the complement of the first nucleotide sequence, wherein said enzyme has cis-prenyltransferase activity.

Additionally the invention provides polypeptides encoded by the isolated nucleic acid molecules of the invention as well as genetic chimera constructed therefrom and recombinant host cells containing and expressing the same.

In another embodiment the invention provides a method of obtaining a nucleic acid molecule encoding a cis-prenyltransferase enzyme comprising:
- a) probing a genomic library with the nucleic acid molecule of the invention;
- b) identifying a DNA clone that hybridizes with the nucleic acid molecule of the invention;
- c) sequencing the genomic fragment that comprises the clone identified in step (b),
  wherein the sequenced genomic fragment encodes a cis-prenyltransferase enzyme.

In similar fashion the invention provides a method of obtaining a nucleic acid molecule encoding a cis-prenyltransferase enzyme comprising:
- a) synthesizing at least one oligonucleotide primer corresponding to a portion of the sequence selected from the group consisting of SEQ ID NOs:3 and 5; and
- b) amplifying an insert present in a cloning vector using the oligonucleotide primer of step (a);
  wherein the amplified insert encodes a portion of an amino acid sequence encoding a cis-prenyltransferase enzyme.

In a preferred embodiment the invention provides a method of altering the level of expression of a plant cis-prenyltransferase protein in a host cell comprising:
- (a) transforming a host cell with the chimeric gene of the invention and;
- (b) growing the transformed host cell produced in step (a) under conditions that are suitable for expression of the chimeric gene resulting in production of altered levels of a plant cis-prenyl-transferase protein in the transformed host cell relative to expression levels of an untransformed host cell.

In a preferred embodiment the invention provides a method for the production of natural rubber compounds comprising:
- a) providing a transformed host cell comprising:
  - (i) suitable levels of isopentenyl pyrophate; and
  - (ii) a cis-prenyltransferase gene selected from the group consisting of SEQ ID NOs: 3 and 5, wherein said genes are operably linked to suitable regulatory sequences; and
- b) growing the transformed host cell of (a) under conditions whereby a natural rubber compound is produced.

Similarly the invention provides a method for the identification of a polypeptide having cis-prenyltransferase activity in a rubber-producing plant comprising:
- (a) obtaining the amino acid sequence of a polypeptide suspected of having cis-prenyltransferase activity; and
- (b) aligning the amino acid sequence of step (a) with the amino acid sequence of a cis-prenyltransferase consensus sequence selected from the group consisting of SEQ ID NO:4, 6, 8, 9, and 10, wherein the alignment shows the presence of conserved domains I, IV, and V (SEQ ID NOs: 38–40).

In an alternate embodiment the invention provides a method for the identification of a polypeptide having cis-prenyltransferase activity in a rubber-producing plant comprising:
- (a) obtaining the amino acid sequence of a polypeptide suspected of having cis-prenyltransferase activity; and
- (b) aligning the amino acid sequence of step (a) with the amino acid sequence of a cis-prenyltransferase consensus sequence selected from the group consisting of SEQ ID NO:4, 6, 8, 9, and 10, wherein the alignment shows a sequence of at least about 50 non-conserved amino acids present between the absolutely conserved tyrosine of Domain IV and the first of the absolutely conserved arginine residue of Domain V.

BRIEF DESCRIPTION OF THE DRAWINGS AND SEQUENCE DESCRIPTIONS

FIG. 1 shows an alignment of the regions between Domains IV and V of cis-prenyltransferases from rubber-producing plants (i.e., russian dandelion, sunflower and *Hevea*) and non-rubber-producing plants and microbes.

Figure 2:
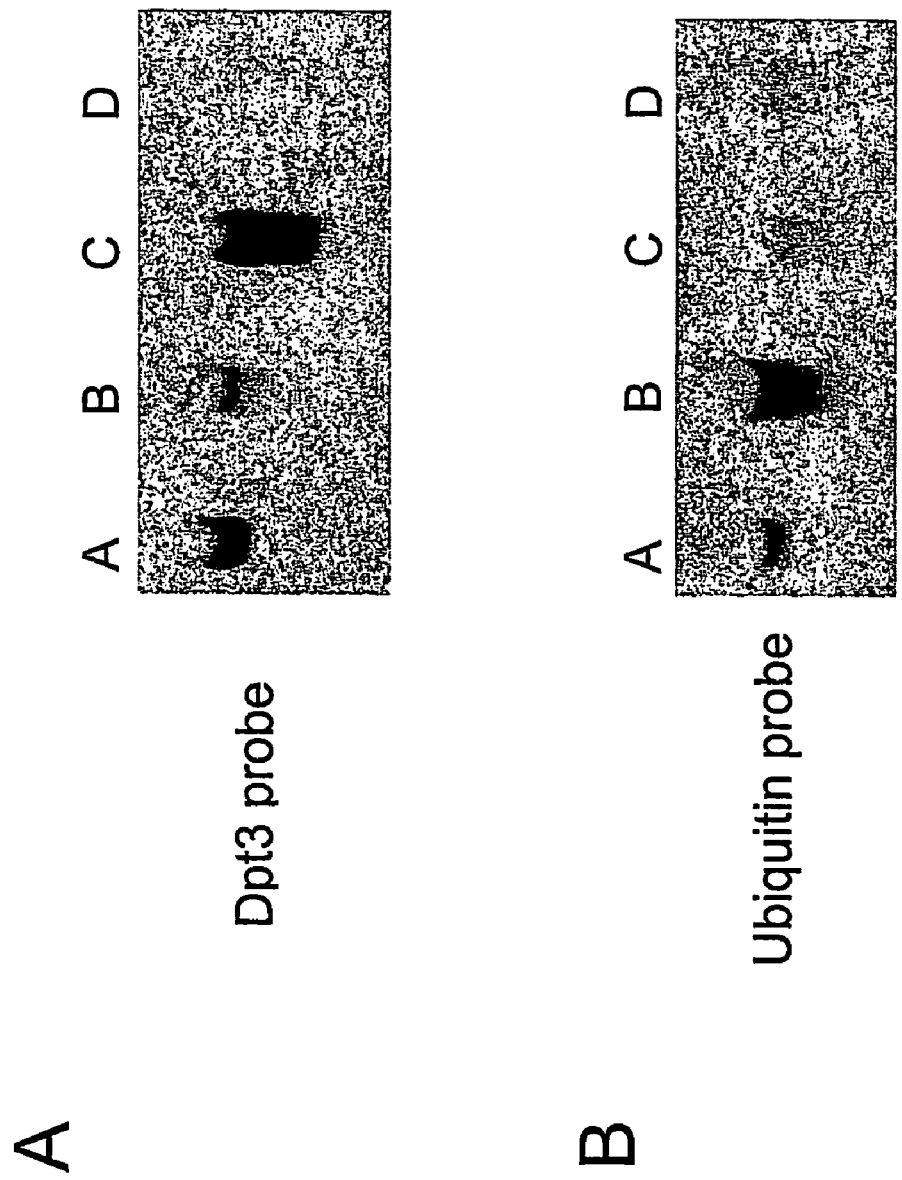
FIG. 2 shows the analysis of expression of the russian dandelion cis-prenyltransferase gene by Northern blotting.

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1–34, 38–40 and 45 are genes or proteins as identified 25 in Table 1.

TABLE 1

Summary of Gene and Protein SEQ ID Numbers

| Clone ID number and Description | Organism | SEQ ID Nucleic acid | SEQ ID Peptide |
|---|---|---|---|
| EST etk1c.pk006.a10 | *Taraxacum kok-saghyz* (russian dandelion) | 1 | — |
| 5'RACE product #3-4 | *Taraxacum kok-saghyz* (russian dandelion) | 2 | — |
| full-length nucleotide sequence for cis-prenyltransferase | *Taraxacum kok-saghyz* (russian dandelion) | 3 | 4 |

TABLE 1-continued

Summary of Gene and Protein SEQ ID Numbers

| Clone ID number and Description | Organism | SEQ ID Nucleic acid | SEQ ID Peptide |
|---|---|---|---|
| (assembled from SEQ ID NO: 1 and SEQ ID NO: 2) | | | |
| hls1c.pk020.m9 | *Helianthus annus* (sunflower) | 5 | 6 |
| ecs1c.pk009.p19 | *Calendula officinalis* (pot marigold) | — | 7 |
| ehb2c.pk001.i10 | *Hevea brasiliensis* | — | 8 |
| ehb2c.pk001.d17 | *Hevea brasiliensis* | — | 9 |
| ehb2c.pk001.o18 | *Hevea brasiliensis* | — | 10 |
| vdb1c.pk001.k23 | *Vitis* sp. (grape) | — | 11 |
| r10n.pk117.i23 | *Oryza sativa* (rice) | — | 12 |
| rr1.pk0050.h8 | *Oryza sativa* (rice) | — | 13 |
| sl1.pk0128.h7 | *Glycine max* (soybean) | — | 14 |
| wdk5c.pk005.f22 | *Triticum aestivum* (wheat) | — | 15 |
| ecs1c.pk009.p19 | *Dimorphotheca sinuata* (african daisy) | — | 16 |
| bacterial undecaprenyl diphosphate synthase | *Micrococcus luteus* | 17 | 18 |
| undecaprenyl phosphate synthase | *Saccharomyces cerevisiae*, strain rer2 | 19 | 20 |
| undecaprenyl phosphate synthase | *Saccharomyces cerevisiae*, strain srt1 | 21 | 22 |
| MUF9.18 | *Arabidopsis* (Genbank Accession No. NM_125443) | — | 23 |
| MJB20.13 | *Arabidopsis* (Genbank Accession No. NM_127311) | — | 24 |
| F26B6.6 | *Arabidopsis* (Genbank Accession No. NM_127905) | — | 25 |
| MZN1.22 | *Arabidopsis* (Genbank Accession No. NM_125267) | — | 26 |
| conserved Domain IV | alignment consensus sequence | — | 27 |
| conserved Domain V | alignment consensus sequence | — | 28 |
| conserved Domain I | consensus sequence from Apfel et al. (J. Bact. 182(2): 483–492 (1999)) | — | 29 |
| conserved Domain II | consensus sequence from Apfel et al. (supra) | — | 30 |
| conserved Domain III | consensus sequence from Apfel et al. (supra) | — | 31 |
| conserved Domain IV | consensus sequence from Apfel et al. (supra) | — | 32 |
| conserved Domain V | consensus sequence from Apfel et al. (supra) | — | 33 |
| Conserved Domain V | Consensus sequence from *Taraxacum kok-saghyz* (russian dandelion) and *Helianthus annus* (sunflower) ESTs | — | 34 |
| conserved Domain I | consensus sequence in rubber-producing species | — | 38 |
| conserved Domain IV | consensus sequence in rubber-producing species | — | 39 |
| conserved Domain V | consensus sequence in rubber-producing species | — | 40 |
| Clone #4-4 (RT-PCR product) | *Taraxacum kok-saghyz* (russian dandelion) latex | — | 45 |

SEQ ID NOs:41 and 42 are the primers Dan5 and Dan6.

SEQ ID NOs: 36, 37, and 44 are the primers NKH46, NKH45, and NKH5.

SEQ ID NO:43 is the primer DegHptS.

SEQ ID NO:35 is the peptide 'ELVISLIVES'.

DETAILED DESCRIPTION OF THE INVENTION

The present invention reports the isolation and characterization of cDNAs corresponding to cis-prenyltransferases from russian dandelion and sunflower. Applications for these genes include the development of novel plant phenotypes possessing greater plant defense responses, crop production, and/or creation of industrial sources of polyisoprenoids (including natural rubber). Furthermore, the present invention provides a technique for readily identifying other cis-prenyltransferase genes from rubber-producing plants.

Definitions

The following definitions are provided for the full understanding of terms and abbreviations used in this specification:

"Polymerase chain reaction" is abbreviated PCR.

"Open reading frame" is abbreviated ORF.

"Expressed sequence tag" is abbreviated EST.

"SDS polyacrylamide gel electrophoresis" is abbreviated SDS-PAGE.

"UPPS" is the abbreviation for the specific undecaprenyl diphosphate synthases isolated from bacteria.

"Dimethyl allyl diphosphate" is abbreviated DMAPP.

"Isopentenyl diphosphate" is abbreviated IPP.

"Geranyl diphosphate" is abbreviated GPP.

"Farnesyl diphosphate" is abbreviated FPP.

"Geranylgeranyl diphosphate" is abbreviated GGPP.

"Polyisoprenoids" refer to a variety of hydrocarbons produced by plants that are built up of isoprene units ($C_5H_8$) (Tanaka, Y. In *Rubber and Related Polyprenols. Methods in Plant Biochemistry*, Dey, P. M. and Harborne, J. B., Eds., Academic Press: San Diego, 1991; Vol. 7, pp 519–536). Those with 45 to 115 carbon atoms and varying numbers of cis- and trans- (Z- and E-) double bonds are termed "polyprenols", while those polyisoprenoids of longer chain length are termed natural "rubbers" (Tanaka, Y. In *Minor Classes of Terpenoids. Methods in Plant Biochemistry*; Dey, P. M. and Harborne, J. B., Eds., Academic: San Diego, 1991; Vol. 7, pp 537–542). There are several-suggested functions for plant polyisoprenoids. For example, terpenoid quinones are most likely involved in photophosphorylation and respiratory chain phosphorylation, while rubbers have been implicated in plant defense against herbivory, by possibly serving to repel and entrap insects and seal wounds in a manner analogous to plant resins. The specific roles of the $C_{45}$–$C_{115}$ polyprenols, however, remain unidentified (although as with most secondary metabolites they too most likely function in plant defense). Short-chain polyprenols may also be involved in protein glycosylation in plants, by analogy with the role of dolichols in animal metabolism.

The term "rubber" encompasses any material that is highly elastic; i.e., the elastic material can be stretched without breaking and will return to its original length on removal of the stretching force. "Natural rubbers" are those rubbers produced by plant species, often (though not always) as a constituent of latex.

The term "plant latex" refers to a milky fluid present in lacticifers, or latex ducts, which seeps out of the plant upon wounding.

The term "cis-prenyltransferase" refers generally to a class of enzymes capable of catalyzing the sequential addition of $C_5$ units to polyprenols and rubbers in cis 1–4 orientation. Two examples of cis-prenyltransferases are the undecaprenyl diphosphate and dehydrodolichyl diphosphate synthase.

The term "initiator molecules" or "initiators" refers to allylic terpenoid diphosphates that are derived from isoprene units (IPP) through the action of prenyltransferases. Examples of common initiators include: dimethylallyldiphosphate (DMAPP), a $C_5$ compound; geranyl diphosphate (GPP), a $C_{10}$ compound; farnesyl diphosphate (FPP), a $C_{15}$ compound; and, geranylgeranyl diphosphate (GGPP), a $C_{20}$ compound.

The term "plant defense response" refers to the ability of a plant to deter tissue damage by insects, pathogens (e.g., fungi, bacteria or viruses), and/or herbivores.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "fragment" refers to a DNA or amino acid sequence comprising a subsequence of the nucleic acid sequence or protein of the present invention. However, an active fragment of the present invention comprises a sufficient portion of the protein to maintain activity.

A nucleic acid molecule is "hybridizable" to another nucleic acid molecule, such as a cDNA, genomic DNA, or RNA molecule, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. (*Molecular Cloning: A Laboratory Manual*, $2^{nd}$ ed.; Cold Spring Harbor Laboratory: Cold Spring Harbor, N.Y., 1989 (hereinafter "Maniatis"), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Maniatis, supra, 9.50–9.51). For hybridizations with shorter nucleic acids, i.e., oligonucleotides, the position of mismatches becomes more important, and the length of the oligonucleotide determines its specificity (see Maniatis, supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including (but not limited to) those described in: 1.)

*Computational Molecular Biology*; Lesk, A. M., Ed.; Oxford University: NY, 1988; 2.) *Biocomputing: Informatics and Genome Projects*; Smith, D. W., Ed.; Academic: NY, 1993; 3.) *Computer Analysis of Sequence Data, Part I*; Griffin, A. M., and Griffin, H. G., Eds.; Humana: NJ, 1994; 4.) *Sequence Analysis in Molecular Biology*; von Heinje, G., Ed.; Academic, 1987; and 5.) *Sequence Analysis Primer*; Gribskov, M. and Devereux, J., Eds.; Stockton: NY, 1991. Preferred methods to determine identity are designed to give the best match between the sequences tested. Methods to determine identity and similarity are codified in publicly available computer programs. Sequence alignments and percent identity calculations may be performed using the AlignX program of the Vector NTI bioinformatics computing suite (InforMax Inc., North Bethesda, Md.). Multiple alignment of the sequences was performed using the Clustal method of alignment (Higgins and Sharp *CABIOS*. 5:151–153 (1989)) with the default parameters (GAP OPENING PENALTY=10, GAP EXTENSION PENALTY=0.1). Default parameters for pairwise alignments using the Clustal method were KTUPLE SIZE=1, GAP PENALTY=3, WINDOW SIZE=5 and NUMBER OF BEST DIAGONALS=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant plant polypeptides as set forth in SEQ ID NOs:4 and 6. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (*Plant Cell* 1:671–680 (1989)).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to. translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLAST P, BLASTN, BLASTX (Altschul et al., *J. Mol. Biol.* 215:403–410 (1990), Vector NTI (InforMax Inc., North Bethesda, Md.) and DNASTAR (DNASTAR Inc., Madison, Wis.). Within the context of this application it will be understood that where sequence analysis software is used for analysis, that the results of the analysis will be based on the "default values" of the program referenced, unless otherwise specified. As used herein "default vales" will mean any set of values or parameters which originally load with the software when first initialized.

The term "conserved domain" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. Conserved domains of are specifically described for the family of cis-prenyltransferases, according to the work of Apfel, C. M. et al. (*J. Bact.* 181(2): 483–492 (1999)).

The term "non-conserved domain" means a set of amino acids, present between conserved domains, which whilst the individual amino acids are not conserved at specific positions along an aligned sequence of evolutionarily related proteins, is recognizable by its presence or absence in aligned sequences of evolutionary related proteins. The presence of such a domain, despite positional non-conservation among its constituent amino acids, indicates that the domain plays a role essential in the structure, the stability, or the activity of a protein, e.g., by increasing the distance between other (conserved) domains. Because they are identified by their presence in aligned sequences of a family of protein homologues, they can be used as identifiers, or "signatures", to determine if a protein with a newly determined sequence belongs to a previously identified protein family or subfamily. In the present invention, non-conserved domains are specifically described for cis-prenyltransferases from rubber-producing plants.

Standard recombinant DNA and molecular cloning techniques used here are well known in the art and are described by: Sambrook, J., Fritsch, E. F. and Maniatis, T., *Molecular Cloning: A Laboratory Manual*; 2nd ed.; Cold Spring Harbor Laboratory: Cold Spring Harbor, N.Y., 1989 (hereinafter "Maniatis"); and by Silhavy, T. J., Bennan, M. L. and Enquist, L. W., *Experiments with Gene Fusions*; Cold Spring Harbor Laboratory: Cold Spring Harbor, N.Y., 1984; and by Ausubel, F. M. et al., *Current Protocols in Molecular Biology*; Greene Publishing Assoc. and Wiley-Interscience (1987).

Cis-Prenyltransferase Sequence Identification

Novel nucleotide sequences have been isolated from the rubber-producing plants *Taraxacum kok-saghyz* (russian dandelion) and *Helianthus annus* (sunflower) encoding gene products involved in the production of natural rubbers. More specifically, these unique plant homologs of microbial cis-prenyltransferase proteins are involved in the synthesis of poly cis-isoprenoids. Classification of the proteins is based on alignments which reveal the presence of five conserved domains, indicative of a cis-prenyltransferase, as described by Apfel et al. (*J. Bact.* 181(2): 483–492 (1999)).

Comparison of the dandelion cis-prenyltransferase nucleotide base and deduced amino acid sequences to public databases reveals that the most similar known sequences are about 50% identical to the amino acid sequence of SEQ ID NO:4 reported herein over a length of 301 amino acids using a Smith-Waterman alignment algorithm (W. R. Pearson, *Comput. Methods Genome Res.*, [Proc. Int. Symp.] (1994), Meeting Date 1992, 111–20. Suhai, S., Ed.; Plenum: New York, N.Y.). Strong correlation was seen between the instant sequences and the cis-prenyltransferase genes and proteins isolated from *Micrococcus luteus* (SEQ ID NOs:17 and 18, encoding undecaprenyl diphosphate synthase; Shimizu, N., et al., *J. Biol. Chem.* 273:19476–19481 (1998)) and *Saccharomyces cerevisiae* (SEQ ID NOs: 19–22).

In like manner, comparison of the sunflower cis-prenyltransferase nucleotide base and deduced amino acid sequences to public databases reveals that the most similar known sequences are about 57% identical to the amino acid sequence of SEQ ID NO: 6 reported herein over a length of 168 amino acids using a Smith-Waterman alignment algorithm. Again, strong correlation was noted between the instant sequences and the cis-prenyltransferase genes and proteins isolated from *Micrococcus luteus* (SEQ ID NOs:17 and 18; Shimizu, N., et al., supra) and *Saccharomyces cerevisiae* (SEQ ID NOs:19–22).

More preferred cis-prenyltransferase amino acid fragments are at least about 70%–80% identical to the sequences herein, where about 80%–90% is preferred. Most preferred are nucleic acid fragments that are at least 95% identical to the amino acid fragments reported herein.

Similarly, preferred cis-prenyltransferase encoding nucleic acid sequences corresponding to the instant ORF's are those encoding active proteins and which are at least 80% identical to the nucleic acid sequences of reported herein. More preferred cis-prenyltransferase nucleic acid fragments are at least 90% identical to the sequences herein. Most preferred are cis-prenyltransferase nucleic acid fragments that are at least 95% identical to the nucleic acid fragments reported herein.

Isolation of Homologs

The nucleic acid fragments of the present invention may be used to isolate cDNAs and genes encoding homologous prenyltransferases from the same or other plant species or from microbial species. Isolating homologous genes using sequence-dependent protocols is well known in the art. Examples of sequence-dependent protocols include (but are not limited to) methods of nucleic acid hybridization and methods of DNA and RNA amplification, as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Acad. Sci, USA* 82:1074, (1985); or strand displacement amplification (SDA), Walker, et al., *Proc. Natl. Acad. Sci. U.S.A.*, 89: 392 (1992)).

For example, other cis-prenyltransferase genes sharing significant homology to those of the instant invention, either as cDNAs or genomic DNAs, could be isolated directly by using all or a portion of the instant nucleic acid fragments as DNA hybridization probes to screen libraries from any desired plant using methodology well known to those skilled in the art. Specific oligonucleotide probes based upon the instant nucleic acid sequences can be designed and synthesized by methods known in the art (Maniatus, supra). Moreover, the entire sequences can be used directly to synthesize DNA probes by methods known to the skilled artisan such as random primers, DNA labeling, nick translation, or end-labeling techniques, or RNA probes using available in vitro transcription systems. In addition, specific primers can be designed and used to amplify a part of (or full-length of) the present sequence. The resulting amplification products can be labeled directly during amplification reactions or labeled after amplification reactions, and used as probes to isolate full length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*; K. E. Davis, Ed.; IRL: Herndon, Va., 1986; pp 33–50); Rychlik, W., In *Methods in Molecular Biology*; PCR Protocols: Current Methods and Applications. White, B. A., Ed.; Humania: Totowa, N.J., 1993; Vol. 15, pp 31–39).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant UPPS homologs.

Alternatively, the second primer sequence may be based upon sequences derived from the cloning vector. For example, the skilled artisan can follow the RACE protocol (Frohman et al., *Proc. Natl. Acad. Sci. USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci., USA* 86:5673 (1989); Loh et al., *Science* 243:217 (1989)). Products generated by the 3' and 5' RACE procedures can be combined to generate full-length cDNAs (Frohman et al., *Techniques* 1:165 (1989)).

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.*, 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt/vol glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Finally, availability of the instant nucleotide and deduced amino acid sequences facilitates immunological screening of DNA expression libraries. Synthetic peptides representing portions of the instant amino acid sequence may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner et al., *Adv. Immunol.* 36:1 (1984); Maniatus, supra).

Recombinant Expression—Plants

It is expected that introduction of chimeric genes encoding the instant cis-prenyltransferase enzymes, under the control of the appropriate promoters, will enable increased production of natural rubbers when an appropriate source of IPP is present in the cell to produce appropriate initiator molecules (DMAPP, GPP, FPP or GGPP). It is contemplated that it will be useful to express the instant genes both in natural host cells as well as heterologous plant hosts.

The nucleic acid fragments of the instant invention may also be used to create transgenic plants in which any of the instant cis-prenyltransferase proteins are present at higher or lower levels than normal, thus permitting modification to the production of natural rubbers. Introduction of the nucleic acid fragments of the instant invention into transgenic plants may have benefit in modifying the rate or timing of rubber production, the amount and/or quality of the rubber produced, and/or the allergenic properties of the resultant rubber. Alternatively, in some applications, it might be desirable to express any of the instant cis-prenyltransferases in specific plant tissues and/or cell types, or during developmental stages in which they would normally not be encountered. The expression of full-length plant cis-prenyltransferase cDNAs yields a mature protein capable of the synthesis of cis-polyisoprenoids from IPP as the substrate. The presence of an initiator allylic isoprenoid diphosphate enhances this activity.

Further, it is contemplated that transgenic plants expressing any of the instant cis-prenyltransferase sequences will have altered or modulated defense mechanisms against various pathogens and natural predators. For example, various latex proteins are known to be antigenic and recognized by IgE antibodies, suggesting their role in immunolgical defense (Yagami et al., *Journal of Allergy and Clinical Immunology*, 101(3): 379–385 (1998)). Additionally it has been shown that a significant portion of the latex isolated from *Hevea brasiliensis* contains chitinases/lysozymes, which are capable of degrading the chitin component of fungal cell walls and the peptidoglycan component of bacterial cell walls (Martin, M. N., *Plant Physiol* (Bethesda), 95 (2): 469–476 (1991)). It is therefore an object of the instant invention to provide transgenic plants having altered, modulated or increased defenses towards various pathogens and herbivores.

Preferred Plant Hosts and Transformation Methods

Preferred plant hosts will be any variety that will support a high production level of the instant cis-prenyltransferase sequences. Suitable plant species include those plant species which produce natural rubber (e.g., *Hevea brasiliensis, Taraxacum* spp.), but are not limited to: tobacco (*Nicotiana* spp.), tomato (*Lycopersicon* spp.), potato (*Solanum* spp.), hemp (*Cannabis* spp.), sunflower (*Helianthus* spp.), sorghum (*Sorghum vulgare*), wheat (*Triticum* spp.), maize (*Zea mays*), rice (*Oryza sativa*), rye (*Secale cereale*), oats (*Avena* spp.), barley (*Hordeum vulgare*), rapeseed (*Brassica* spp.), broad bean (*Vicia faba*), french bean (*Phaseolus vulgaris*), other bean species (*Vigna* spp.), lentil (*Lens culinaris*), soybean (*Glycine max*), arabidopsis (*Arabidopsis thaliana*), guayule (*Parthenium argentatum*), cotton (*Gossypium hirsutum*), petunia (*Petunia hybrida*), flax (*Linum usitatissimum*), and carrot (*Daucus carota sativa*).

One skilled in the art recognizes that the expression level and regulation of a transgene in a plant can vary significantly from line to line. Thus, one has to test several lines to find one with the desired expression level and regulation.

A variety of techniques are available and known to those skilled in the art for introduction of constructs into a plant cell host. These techniques include transformation with DNA employing *A. tumefaciens* or *A. rhizogenes* as the transforming agent, electroporation, particle acceleration, etc. (see, for example, EP 295959 and EP 138341). It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciofti et al., *Bio/Technology* 3:241 (1985); Byme et al., *Plant Cell, Tissue and Organ Culture* 8:3 (1987); Sukhapinda et al., *Plant Mol. Biol.* 8:209–216 (1987); Lorz et al., *Mol. Gen. Genet.* 199:178 (1985); Potrykus, *Mol. Gen. Genet.* 199:183 (1985); Park et al., *J. Plant Biol.* 38(4):365–71 (1995); Hiei et al., *Plant J.* 6:271–282 (1994)). The use of T-DNA to transform plant cells has received extensive study and is amply described (EP 120516; Hoekema, In: *The Binary Plant Vector System*, Offset-drukkerij Kanters B. V.; Alblasserdam (1985), Chapter V; Knauf, et al., *Genetic Analysis of Host Range Expression by Agrobacterium*, In: *Molecular Genetics of the Bacteria-Plant Interaction*, Puhler, A. Ed.; Springer-Verlag: New York, 1983, p 245; and An, et al., *EMBO J.* 4:277–284 (1985)). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (see Fromm et al., *Nature* (London) 319:791 (1986)) or high-velocity ballistic bombardment with metal particles coated with the nucleic acid constructs (see Kline et al., *Nature* (London) 327:70 (1987), and see U.S. Pat. No. 4,945,050). Once transformed, the cells can be regenerated by those skilled in the art. Of particular relevance are the recently described methods to transform foreign genes into commercially important crops, such as rapeseed (see De Block et al., *Plant Physiol.* 91:694–701 (1989)), sunflower (Everett et al., *Bio/Technology* 5:1201 (1987)), soybean (McCabe et al., *Bio/Technology* 6:923 (1988); Hinchee et al., *Bio/Technology* 6:915 (1988); Chee et al., *Plant Physiol.* 91:1212–1218 (1989); Christou et al., *Proc. Natl. Acad. Sci USA* 86:7500–7504 (1989); EP 301749), rice (Hiei et al., *Plant J.* 6:271–282 (1994)), corn (Gordon-Kamm et al., *Plant Cell* 2:603–618 (1990); Fromm et al., *Biotechnology* 8:833–839 (1990)), and *Hevea* (Yeang, H. Y., et al., Rubber Latex as an Expression System for High-value Proteins. In, Engineering Crop Plants for Industrial End Uses. Shewry, P. R., Napier, J. A., David, P. J., Eds.; Portland: London, 1998; pp 55–64).

Transgenic plant cells are then placed in an appropriate selective medium for selection of transgenic cells that are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide, or the like). The particular marker used will allow for selection of transformed cells as compared to cells lacking the DNA that has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region that is not native to the gene from which the transcription-initiation-region is derived.

To confirm the presence of the transgenes in transgenic cells and plants, a Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts may be harvested, and/or the seed collected. The seed may serve as a source for growing additional plants with tissues or parts having the desired characteristics.

Construction of Chimeric Genes for Transformation

Overexpression of the instant cis-prenyltransferases may be accomplished by first constructing chimeric genes in which the coding region is operably-linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric gene may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences or the present invention should be capable of promoting expression of the present gene product. High level plant promoters that may be used in this invention, for example, include the promoter of the small subunit (ss) of the ribulose-1,5-bisphosphate carboxylase from soybean (Berry-Lowe et al., *J. Molecular and App. Gen.*, 1:483–498 (1982)), and the promoter of the chlorophyll a/b binding protein. These two promoters are known to be light-induced in plant cells (see, for example, *Genetic Engineering of*

*Plants, an Agricultural Perspective*, A. Cashmore, Ed.; Plenum: NY, 1983; pp 29–38; Coruzzi, G. et al., *The Journal of Biological Chemistry*, 258:1399 (1983); and Dunsmuir, P. et al., *Journal of Molecular and Applied Genetics*, 2:285 (1983)).

Plasmid vectors comprising the instant chimeric genes can then be constructed. The choice of a plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus that multiple events must be screened in order to obtain lines displaying the desired expression level and pattern. Such screening may be accomplished by Southern analysis of DNA blots (Southern, *J. Mol. Biol.* 98: 503 (1975)), Northern analysis of mRNA expression (Kroczek, *J. Chromatogr. Biomed. Appl.*, 618(1–2): 133–145 (1993)), Western analysis of protein expression, or phenotypic analysis.

For some applications it may be useful to direct the cis-prenyltransferase proteins to different cellular compartments or to facilitate their secretion from the cell. It is thus envisioned that the chimeric genes described above may be further modified by the addition of appropriate intracellular or extracellular targeting sequences to their coding regions (and/or with targeting sequences that are already present removed). These additional targeting sequences include chloroplast transit peptides (Keegstra et al., *Cell* 56:247–253 (1989)), signal sequences that direct proteins to the endoplasmic reticulum (Chrispeels et al., *Ann. Rev. Plant Phys. Plant Mol.* 42:21–53 (1991)), and nuclear localization signal (Raikhel et al., *Plant Phys.* 100:1627–1632 (1992)). While the references cited give examples of each of these, the list is not exhaustive and more targeting signals of utility may be discovered in the future which are useful in the invention.

Recombinant Expression—Microbial

The genes and gene products of the instant sequences may also be produced in heterologous host cells, particularly in the cells of microbial hosts. Production of natural rubbers in microbial hosts will be useful when an appropriate source of IPP is present in the cell to produce appropriate initiator molecules (DMAPP, GPP, FPP or GGPP). Expression in recombinant microbial hosts may be useful for the expression of various pathway intermediates; or for the modulation of pathways already existing in the host for the synthesis of new products heretofore not possible using the host. Additionally, recombinant expression may be useful for the preparation of antibodies to the cis-prenyltransferase protein by-methods well known to those skilled in the art. The antibodies would be useful for detecting the instant cis-prenyltransferase proteins in situ in cells or in vitro in cell extracts.

Preferred Microbial Hosts and Transformation Methods

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any bacteria, yeast, and filamentous fungi will be suitable hosts for expression of the present nucleic acid fragments. Because transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, or saturated hydrocarbons such as methane or carbon dioxide (in the case of photosynthetic or chemoautotrophic hosts). However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include but are not limited to bacterial (e.g., *Bacillus, Escherichia, Salmonella* and *Shigella*), fungal, or yeast species (e.g., *Aspergillus, Saccharomyces, Pichia, Candida* and *Hansenula*).

Methods for the transformation of such hosts and the expression of foreign proteins are well known in the art and examples of suitable protocols may be found In *Manual of Methods for General Bacteriology*; Gerhardt et al., Eds.; American Society for Microbiology: Washington, D.C., 1994 or In *Biotechnology: A Textbook of Industrial Microbiology*, 2$^{nd}$ ed., Brock, T. D., Ed.; Sinauer Associates: Sunderland, Mass., 1989.

Construction of Chimeric Genes for Transformation

Microbial expression systems and expression vectors containing regulatory sequences that direct high level expression of foreign proteins are well known to those skilled in the art. Any of these could be used to construct chimeric genes for production of the instant cis-prenyltransferases. These chimeric genes could then be introduced into appropriate microorganisms via transformation to provide high level expression of the instant cis-prenyltransferase proteins.

Vectors or cassettes useful for the transformation of suitable microbial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene that harbors transcriptional initiation controls and a region 3' of the DNA fragment that controls transcriptional termination. It is most preferred when both control regions are derived from genes homologous to the transformed host cell, although it is to be understood that such control regions need not be derived from the genes native to the specific species chosen as a production host.

Initiation control regions or promoters that are useful to drive expression of the instant cis-prenyltransferases in the desired microbial host cell are numerous and familiar to those skilled in the art. Virtually any promoter capable of driving these genes is suitable for the instant invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters (useful for expression in *Bacillus*).

Termination control regions may also be derived from various genes native to the preferred hosts. Optionally, a termination site may be unnecessary; however, it is most preferred if included.

Industrial Production in Microbial Hosts

Where commercial production of the instant enzymes are desired a variety of culture methodologies may be applied. For example, large-scale production of a specific gene product overexpressed from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in *Biotechnology: A Textbook of Industrial Microbiology*, $2^{nd}$ ed., Brock, T. D., Ed.; Sinauer Associates: Sunderland, Mass., 1989; or Deshpande, Mukund V., *Appl. Biochem. Biotechnol.*, 36: 227 (1992), herein incorporated by reference.

Commercial production of the instant cis-prenyltransferases and their proteins may also be accomplished with a continuous culture. Continuous cultures are open systems where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products, or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include, but are not limited to: monosaccharides (e.g., glucose and fructose), oligosaccharides (e.g., lactose or sucrose), polysaccharides (e.g., starch, cellulose, or mixtures thereof), and unpurified mixtures from renewable feedstocks (e.g., cheese whey permeate, cornsteep liquor, sugar beet molasses, and barley malt). Additionally the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], $7^{th}$ ed.; Murrell, J. Collin; Kelly, Don P., Eds.; Intercept: Andover, UK, 1993; pp 415–32). Similarly, various species of *Candida* will metabolize alanine or oleic acid (Sulter et al., *Arch. Microbiol*. 153:485–489 (1990)). Hence it is contemplated that the source of carbon utilized in the present invention may encompass a wide variety of carbon containing substrates and will only be limited by the choice of host organism.

Pathway Engineering

Knowledge of the sequence of the present genes will be useful in manipulating the polyisoprenoid biosynthetic pathways in any organism having such a pathway and particularly in other rubber producing plants. Methods of manipulating genetic pathways are common and well known in the art. Selected genes in a particularly pathway may be up-regulated or down-regulated by variety of methods. Additionally, competing pathways in an organism may be eliminated or sublimated by gene disruption and similar techniques.

Once a key genetic pathway has been identified and sequenced, specific genes may be up-regulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565, 350; Zarling et al., PCT/US93/03868).

Alternatively, it may be necessary to reduce or eliminate the expression of certain genes in the target pathway or in competing pathways that may serve as competing sinks for energy or carbon. Methods of down-regulating genes for this purpose have been explored.

For example, where sequence of the gene to be disrupted is known, one of the most effective methods for gene down-regulation is targeted gene disruption where foreign DNA is inserted into a structural gene so as to disrupt transcription. This can be effected by the creation of genetic cassettes comprising the DNA to be inserted (often a genetic marker) flanked by sequences having a high degree of homology to a portion of the gene to be disrupted. Introduction of the cassette into the host cell results in insertion of the foreign DNA into the structural gene via the native DNA replication mechanisms of the cell (see for example Hamilton et al. *J. Bacteriol.* 171:4617–4622 (1989); Balbas et al. *Gene* 136:211–213 (1993); Gueldener et al. *Nucleic Acids Res.* 24:2519–2524 (1996); and Smith et al. *Methods Mol. Cell. Biol.* 5:270–277(1996)).

Alternative methods are available to reduce or eliminate expression of genes encoding the instant polypeptides, if desirable in plants for some applications. In order to accomplish this, a chimeric gene designed for co-suppression of the instant polypeptide can be constructed by linking a gene or gene fragment encoding that polypeptide to plant promoter sequences. Antisense technology requires that a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan. Nonetheless, either the co-suppression or antisense chimeric genes could be introduced into plants via transformation wherein expression of the corresponding endogenous genes is reduced or eliminated.

Finally, one recent variation upon "classical" antisense and cosuppression methodologies is embodied in WO 02/00904, published on Jan. 3, 2002. Specifically, it was found that suitable nucleic acid sequences and their reverse complement can be used to alter the expression of any mRNA encoding a protein of interest which is in proximity to the suitable nucleic acid sequence and its reverse complement. Surprisingly, the suitable nucleic acid sequence and its reverse complement can be either unrelated to any endogenous RNA in the host or can be encoded by any nucleic acid sequence in the genome of the host provided that the nucleic acid sequence does not encode any target mRNA or any sequence that is substantially similar to the target mRNA. A preferred artificial and non-naturally occurring, sequence is that encoded by the peptide "ELVISLIVES" (SEQ ID NO:35). This approach permits a very efficient and robust approach to achieving single, or multiple, gene co-suppression using single plasmid transformation.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression or similar methodologies thereto (U.S. Pat. No. 5,190,931; U.S. 5,107,065; U.S. 5,283,323; WO 02/00904). An antisense or cosuppression construct would act as a dominant negative regulator of gene activity. While conventional mutations can yield negative regulation of gene activity, these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations that may have an effect in all tissues in which a mutant gene is ordinarily expressed.

A person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one that allows large numbers of samples to be processed rapidly, since it will be expected that a large number of transformants will be negative for the desired phenotype.

Although targeted gene disruption and antisense technology offer effective means of down-regulating genes where the sequence is known, other less specific methodologies have been developed that are not sequence based. For example, cells may be exposed to UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See, for example: Thomas D. Brock in *Biotechnology: A Textbook of Industrial Microbiology*, $2^{nd}$ ed., Brock, T. D., Ed.; Sinauer Associates: Sunderland, Mass., 1989; or Deshpande, Mukund V., *Appl. Biochem. Biotechnol.*, 36: 227 (1992).

Another non-specific method of gene disruption is the use of transposable elements or transposons. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass., based upon the bacterial transposon Tn7; and the Ez::TN Transposon Insertion Systems, available from Epicentre Technologies, Madison, Wis., based upon the Tn5 bacterial transposable element).

Protein Engineering

It is contemplated that the instant nucleotides may be used to produce gene products having enhanced or altered activity. For example, the mutation of trans-prenyltransferases such as farnesyl diphosphate synthase to a form capable of generating a different and longer product (geranylgeranyl diphosphate) than the unmodified enzyme has been demonstrated (Ohnuma, S.-I. et al., *J. Biol. Chem.*, 271(17): 10087–10095 (1996)). Various methods are known for mutating a native gene sequence to produce a gene product with altered or enhanced activity including, but not limited to:

1.) error prone PCR (Melnikov et al., *Nucleic Acids Research*, 27(4): 1056–1062 (Feb. 15, 1999));
2.) site directed mutagenesis (Coombs et al., *Proteins*; Angeletti, Ruth Hogue, Ed.; Academic: San Diego, Calif., 1998; pp 259–311, 1 plate); and
3.) "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to (or difference to) the gene of interest. This pool of fragments will then be denatured and reannealed to create a mutated gene. The mutated gene is then screened for altered activity.

The instant plant sequences of the present invention may be mutated and screened for altered or enhanced activity by this method. The sequences should be double stranded and can be of various lengths ranging from 50 bp to 10 kb. The sequences may be randomly digested into fragments ranging from about 10 bp to 1000 bp, using restriction endonucleases well known in the art (Maniatis, supra). In addition to the instant plant sequences, populations of fragments that are hybridizable to all or portions of the microbial sequence may be added. Similarly, a population of fragments that are not hybridizable to the instant sequence may also be added. Typically these additional fragment populations are added in about a 10 to 20 fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from about 80° C. to 100° C. The nucleic acid fragments may be reannealed by cooling. Preferably the temperature is from about 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTPs (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocols (Manatis, supra).

Furthermore, a hybrid protein can be assembled by fusion of functional domains using the gene shuffling (exon shuffling) method (Nixon et al., *PNAS*, 94:1069–1073 (1997)). The functional domain of the instant gene can be combined with the functional domain of other genes to create novel enzymes with desired catalytic function. A hybrid enzyme may be constructed using PCR overlap extension methods and cloned into various expression vectors using the techniques well known to those skilled in art.

Other Applications

The instant cis-prenyltransferase proteins can be used as a target to facilitate the design and/or identification of inhibitors of cis-prenyl-transferases that may be useful as herbicides or fungicides. This could be achieved either through the rational design and synthesis of potent functional inhibitors that result from structural and/or mechanistic information that is derived from the purified instant plant proteins, or through random in vitro screening of chemical libraries. It is anticipated that significant in vivo inhibition of the cis-prenyltransferase proteins described herein may severely cripple cellular metabolism and likely result in plant (or fungal) death.

All or a portion of the nucleic acid fragments of the instant invention may also be used as probes for genetically and physically mapping the genes that they are a part of, and as markers for traits linked to expression of the instant cis-prenyltransferases. Such information may be useful in plant breeding in order to develop lines with desired phenotypes. For example, the instant nucleic acid fragments may be used as restriction fragment length polymorphism (RFLP) markers. Southern blots (Maniatus, supra) of restriction-digested plant genomic DNA may be probed with the nucleic acid fragments of the instant invention. The resulting banding patterns may then be subjected to genetic analyses using computer programs such as MapMaker (Lander et al., *Genomics* 1:174–181 (1987)) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequences in the genetic map previously obtained using this population (Botstein et al., *Am. J. Hum. Genet.* 32:314–331 (1980)).

The production and use of plant gene-derived probes for use in genetic mapping is described by Bernatzky et al. (*Plant Mol. Biol. Reporter* 4:37–41 (1986)). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al., *Nonmammalian Genomic Analysis: A Practical Guide*; Academic, 1996; pp. 319–346 and references cited therein).

In another embodiment, nucleic acid probes derived from the instant nucleic acid sequences may be used in direct fluorescence in situ hybridization (FISH) mapping. Although current methods of FISH mapping favor use of large clones, improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian et al., *J. Lab. Clin. Med.* 114:95–96 (1989)), polymorphism of PCR-amplified fragments (CAPS; Sheffield et al., *Genomics* 16:325–332 (1993)), allele-specific ligation (Landegren et al., *Science* 241:1077–1080 (1988)), nucleotide extension reactions (Sokolov et al., *Nucleic Acid Res.* 18:3671 (1990)), Radiation Hybrid Mapping (Walter et al., *Nature Genetics* 7:22–28 (1997)), and Happy Mapping (Dear et al., *Nucleic Acid Res.* 17:6795–6807 (1989)). For these methods, the sequence of a nucleic acid fragment is used to design and produce primer pairs for use in the amplification reaction or in primer extension reactions. The design of such primers is well known to those skilled in the art. In methods using PCR-based genetic mapping, it may be necessary to identify DNA sequence differences between the parents of the mapping cross in the region corresponding to the instant nucleic acid sequence. This, however, is generally not necessary for mapping methods.

Loss of function-mutant phenotypes may be identified for the instant cDNA clone either by targeted gene disruption protocols or by identifying specific mutants for this gene contained in a population of plants carrying mutations in all possible genes (e.g., Ballinger et al., *Proc. Natl. Acad. Sci. USA* 86:9402 (1989); Koes et al., *Proc. Natl. Acad. Sci. USA* 92:8149 (1995); Bensen et al., *Plant Cell* 7:75 (1995)). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen et al., supra). The amplification of a specific DNA fragment with these primers indicates the insertion of the mutation tag element in or near the plant gene encoding the cis-prenyltransferase protein. Alternatively, the instant nucleic acid fragments may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a cis-prenyltransferase protein can be identified and obtained. This mutant plant can then be used to determine or confirm the natural function of the cis-prenyltransferase gene product.

DESCRIPTION OF PREFERRED EMBODIMENTS

Numerous studies have examined prenyltransferases capable producing long-chain isoprenoids with trans-chain configuration. However, identification of those prenyltransferases that condense isoprene units in the cis-configuration are less well studied. Undecaprenyl pyrophosphate synthetase (di-trans,poly-cis-decaprenylcistransferase, or Upp synthetase; EC 2.5.1.31) was first isolated from *E. coli* in 1999 by Apfel et al. (*J. Bact.* 181(2): 483–492). Apfel et al. also published an alignment of the deduced amino acid sequence of the *E. coli* Upp synthase gene with a number (28) of other publicly-available sequences from bacteria, yeast (*Saccharomyces cerevisiae*) and one eukaryote (*Caenorhabditis elegans*), which revealed five conserved domains. These domains are shown below:

```
                                                (SEQ ID NO:29)
Domain I:   HxxxxMDGN(RG)R(WYF)A;

(SEQ ID NO:30)
Domain II:  GHxxG;

(SEQ ID NO:31)
Domain III: (TS)xxAFS(ST)ENxxRxxxEVxxLMxL;

(SEQ ID NO:32)
Domain IV:  AxxYGGRx(DE)(LIVM)xxA;

(SEQ ID NO:33)
Domain V:   (DE)LxIRT(SAG)GExRxSNF(ML)(LMP)WQxxY
            (SAT)ExxFxxxxWP(DE)F.
```

Apfel et al. predicts that these conserved domains, as well as a few single conserved amino acids outside of the conserved domains, likely represent the active site of the protein.

In the present invention, the Applicants describe unique plant homologs of microbial cis-prenyltransferase proteins that are involved in the synthesis of poly-cis-isoprenoids. More specifically, these cis-prenyltransferases have been isolated from the natural rubber producing plants russian dandelion (*Taraxacum kok-saghyz*) and sunflower (*Helianthus annus*). Comparison of these cDNA sequences to the GenBank database using the BLAST algorithm, well known to those skilled in the art, reveals that these cis-prenyltransferase proteins belong to the broad family of known cis-prenyltransferase genes. This conclusion is additionally based on the presence of conserved domains I–V, as described by Apfel et al., supra.

Further analysis of cis-prenyltransferase sequences, however, reveals surprisingly unique characteristics that are specific for those cis-prenyltransferases isolated from rubber-producing plants. More specifically, the Applicants describe:

1. Modified sequences of conserved domains I, IV, and V, with respect to Apfel et al., that are indicative of the subfamily of cis-prenyltransferases associated with rubber-producing plants; and 2. A unique non-conserved domain between conserved domain IV and V, that is present in cis-prenyltransferases from rubber-producing plants and that is absent in cis-prenyltransferases from other plants.

These two identifying characteristics are thus diagnostic for cis-prenyltransferases from rubber-producing plants and will permit rapid identification of cis-prenyltransferases from rubber-producing species.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used here are well known in the art and are described by Sambrook et al., *Molecular Cloning: A Laboratory Manual*, 2$^{nd}$ ed., Cold Spring Harbor Laboratory: Cold Spring Harbor, N.Y., 1989 (hereinafter "Maniatus"); and by T. J. Silhavy, M. L. Bennan, and L. W. Enquist, *Experiments with Gene Fusions*, Cold Spring Harbor Laboratory: Cold Spring Harbor, N.Y., 1984; and by Ausubel et al., *Current Protocols in Molecular Biology*, published by Greene Publishing Assoc. and Wiley-Interscience, 1987. Nucleotide and amino acid percent identity and similarity comparisons were made using the BLAST (Basic Local Alignment Search Tool; Altschul et al., *J. Mol. Biol.* 215:403–410 (1993); algorithms and also the Vector NTI suite of programs, applying default parameters unless indicated otherwise. The meaning of abbreviations is as follows: "sec" means second(s), "min" means minute(s), "h" means hour(s), "d" means day(s), "µL" means microliter, "mL" means milliliters, "L" means liters, "µM" means micromolar, "mM" means millimolar, "M" means molar, "mmol" means millimole(s), "µmole" mean micromole", "g" means gram, "µg" means microgram, "ng" means nanogram, "U" means units, "bp" means base pairs, and "kB" means kilobase.

Example 1

Preparation of cDNA Libraries from Russian Dandelion and Sunflower

This example describes the preparation of two cDNA libraries, one from russian dandelion latex tissue and one from sunflower leaf tissue. These libraries were then used for sequencing of expressed sequencing tags (ESTs).

Library Construction for Russian Dandelion, *Taraxacum kok-saghyz*

A cDNA library representing mRNAs from russian dandelion latex tissue was prepared, using the SMART cDNA Library Construction Kit (Clontech, Palo Alto, Calif.). The cDNAs were introduced into plasmid vectors by first preparing the cDNA library in λTriplEx2 vectors and then converted into a plasmid library (Clontech). Upon conversion, cDNA inserts were contained in the plasmid vector pTriplEx2 and plasmid DNAs were prepared from randomly selected bacterial colonies. Amplified insert DNAs or plasmid DNAs were sequenced in dye-primer sequencing reactions to generate partial cDNA sequences (expressed sequence tags or "ESTs"; see Adams et al., *Science* 252: 1651–1656 (1991)). The resulting ESTs were analyzed using a Perkin Elmer Model 377 fluorescent sequencer.

Library Construction for Sunflower, *Helianthus annus*

SMF3 Sunflower plants were grown in the greenhouse for 4 weeks and then transferred to a growth chamber with a 12 hr photoperiod, at 22° C. and 80% relative humidity. The sunflower pathogen, *Schlerotinia sclerotiorum* (isolate 255M), was maintained on a PDA plate at 20° C. in the dark. When the sunflower plants were 6 weeks old, they were inoculated with *Sclerotinia*-infested carrot plugs with active growing mycelia. For each plant, three petioles were inoculated and wrapped with parafilm. Leaf tissue samples were collected, immediately frozen in liquid nitrogen, and stored at −80° C.

Total RNA was isolated from this tissue using TriPure Reagent (Roche Applied Science, Indianapolis, Ind.). Subsequently, mRNAs were isolated using a mRNA purification kit (Invitrogen, Carlsbad, Calif.). A cDNA library representing mRNAs from sunflower leaf tissue infected with the pathogen *S. scierotiorum* was prepared, using the Lamda ZAPII-cDNA synthesis kit (Stratagene, LaJolla, Calif.). Once the cDNA inserts were in plasmid vectors, plasmid DNAs were prepared from randomly selected bacterial colonies containing recombinant pBluescript plasmids. Amplified insert DNAs or plasmid DNAs were sequenced in dye-primer sequencing reactions to generate partial cDNA sequences (expressed sequence tags or "ESTs"; see Adams et al., supra. The resulting ESTs were analyzed using a Perkin Elmer Model 377 fluorescent sequencer.

Example 2

Identification and Characterization of Cis-prenyltransferases

This Example describes the methodology utilized to conduct BLAST analyses on each EST sequenced in Example 1 and the identification of two novel cis-prenyltransferase genes.

Specifically, all sequences from Example 1 were identified by conducting BLAST (Basic Local Alignment Search Tool; Altschul, S. F., et al., (1993) *J. Mol. Biol.* 215: 403–410; searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases).

The cDNA sequences were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. *Nature Genetics* 3:266–272 (1993)) provided by the NCBI.

cDNAs were further identified by searches of the database using the TBLASTN algorithm provided by the National Center for Biotechnology Information (NCBI) and short fragments of conserved sequence present in known cis-prenyltransferases (conserved domains I–V, as described by .Apfel et al., *J. Bacteriol.* 81:483–492 (1999)). These sections of conserved sequence were expected to be diagnostic for the cis-prenyltransferase family of enzymes.

The results of these BLAST comparisons are given below in Table 2 for the ESTs of the present invention. Table 2 summarizes the sequence to which each EST potentially encoding a cis-prenyltransferase has the most similarity (presented as % similarities, % identities, and expectation values). The table displays data based on the BLASTXnr algorithm with values reported in expect values. The Expect value estimates the statistical significance of the match, specifying the number of matches, with a given score, that are expected in a search of a database of this size absolutely by chance.

TABLE 2

ESTs Potentially Encoding Cis-Prenyltransferases, as Identified by Automated BLAST Searches of Public Databases

| ORF Name | EST and Organism of Isolation | Similarity Identified | SEQ ID NOs | % Identity[a] | % Similarity[b] | E-value[c] | Citation |
|---|---|---|---|---|---|---|---|
| 1 | Cis-prenyltransferase etk1c.pk006.a10 (*Taraxacum kok-saghyz*) | *H. brasiliensis* cis-prenyltransferase (hcpt-3 mRNA, partial cds) (AB061235) | 1, 2 | 44 | 64 | $4.4 \times 10^{-20}$ | Asawatreratanakul, K., Zhang, Y. W., Wititsuwannakul, R. and Koyama, T., direct submission |
| 2 | Cis-prenyltransferase hls1c.pk020.m9 (*Helianthus annus*) | *H. brasiliensis* cis-prenyltransferase (AB061237) | 5, 6 | 57 | 81 | $2.0 \times 10^{-32}$ | Asawatreratanakul, K., Zhang, Y. W., Wititsuwannakul, R. and Koyama, T., direct submission |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

The russian dandelion EST was found to have the highest homology (44% identity) to a partial clone of a cis-prehyltransferase gene of *H. brasiliensis* (Accession Number AB061235), using automated BLAST searches against sequences deposited in the public databases (Table 2). To further analyze the dandelion EST sequence, it was translated and aligned with other full-length cis-prenyltransferase genes. Using this approach the sequence exhibited 30.5% identity with its closest homolog, the Hevea Hpt1 gene product (SEQ ID NO:8)

The sunflower EST sequence was found to have the highest homology (57% identity) to a full-length clone of a cis-prenyltransferase gene of *H. brasiliensis* (Accession Number AB061237), using automated BLAST searches against sequences deposited in the public databases (Table 2). Comparison of the sunflower EST sequence (SEQ ID NO:6) to the Hevea Hpt1 gene product (SEQ ID NO:8) determined that there was 24.4% identity to Hpt1.

In addition to the homology both ESTs exhibited with other known cis-prenyltransferase genes, the russian dandelion and sunflower EST also was found to possess significant homology to one of the five conserved domains reported by Apfel et al. (supra). Specifically, both ESTs possesed the amino acid sequence:
DILVRSSGETRLSNFLLWQTTNCVLYSPKALWPEM
(SEQ ID NO: 34), which shares homology with Domain V of Apfel et al. (supra).

Further analysis of the DNA alignments, however, revealed that both the russian dandelion and sunflower EST sequences did not encode full length ORFs. The 5' end of the russian dandelion cDNA appeared to be missing over 201 bp, while the sunflower cDNA appeared to be missing over 192 bp of its 5' sequence. The full-length cis-prenyltransferase cDNA sequences, therefore, could not be determined, and the low % homologies in alignments with known cis-prenyltransferases are due to use of partial cDNAs.

Example 3

Acquisition of Full-length Russian Dandelion Cis-prenyltransferase cDNA

This Example describes the methodology used to isolate the full-length cDNA for the russian dandelion cis-prenyltranferase, since the dandelion sequence analyzed in Example 2 appeared to be missing the 5' end when aligned with known full-length cis-prenyltransferases.

Rapid amplification of cDNA ends (RACE) was performed to obtain the 5' end sequence of the russian dandelion cis-prenyltransferase gene, using the FirstChoice RLM-RACE Kit (Ambion, Austin, Tex.). The gene-specific oligonucleotides used for the outer 5'RLM-RACE PCR was NKH46 (SEQ ID NO:36) and for the inner 5'RLM-RACE PCR was NKH45 (SEQ ID NO:37). Several PCR products were obtained by RACE. These products were then cloned using a TOPO TA-cloning kit (Invitrogen, Carlsbad, Calif.) and transformed into *E. coli*. Plasmids were isolated and purified using QIAFilter cartridges (Qiagen, Valencia, Calif.).

Sequences were generated on an ABI Automatic sequencer using dye terminator technology, using a combination of vector-specific primers, and editing was performed in Vector NTI (InforMax Inc., North Bethesda, Md.). To aid in the analysis of RACE PCR products, the design of the primers used in RACE was such that the amplified 5' end RACE products contain at least 200 bp from the 5' end of the known partial cDNA sequence. Thus, the sequence of the PCR products obtained by RACE were aligned with the cDNA sequence of the russian dandelion cis-prenyltransferase EST in Vector NTI's Contig Express. Those PCR products that did not align with at least 200 bp of the partial cDNA sequence of the russian dandelion cis-prenyltransferase EST were discarded. One clone (#3-4) obtained by 5' RACE contained 258 bp of sequence (SEQ ID NO:2) identical to that of the EST representing the partial russian dandelion cis-prenyltransferase cDNA, verifying that this RACE product was genuine. This allowed the sequence of the full-length russian dandelion cDNA clone (SEQ ID NO:3) to be assembled in Vector NTI's ContigExpress program. The deduced full-length amino acid sequence (SEQ ID NO:4) exhibited 49.8% identity (61.2% similarity) with that of the Hevea Hpt1 gene product (SEQ ID NO:8).

Example 4

Identification of a Diagnostic Non-conserved Domain in Rubber-producing Cis-prenyltransferases This Example describes the identification of a non-conserved domain in the cis-prenyltransferases of rubber-producing plants, discovered from alignments of three Hevea cis-prenyltransferases (SEQ ID NOs:8–10), the russian dandelion cis-prenyltransferase (SEQ ID NO:4), and the sunflower cis-prenyltransferase (SEQ ID NO:6). This domain will be a useful tool to rapidly identify cis-prenyltransferases likely to be involved in long-chain rubber biosynthesis in the future. Additionally, modified conserved domains were identified for cis-prenyltransferases from rubber-producing plant species, corresponding to the conserved domains of Apfel et al. (J. Bacteriol. 81:483–492 (1999)).

An alignment of the deduced amino acid sequences of the cDNAs of the instant invention with various known cis-prenyltransferases (WO 01/21650) was created, using the CLUSTALW program within the VECTOR NTI suite of programs (full alignment not shown). Specifically, aligned sequences include those from: 1.) rubber-producing plants (i.e., russian dandelion, sunflower and Hevea, corresponding to SEQ ID NOs:4, 6 and 8–10); 2.) non-rubber-producing plants (i.e., rice, marigold, grape, soybean, wheat, African daisy, and Arabidopsis, corresponding to SEQ ID NOs:12, 7, 11, 14, 15, 16, and 23–26); and 3.) microbes (i.e., Micrococcus and Saccharomyces, corresponding to SEQ ID NOs: 18 and 20 and 22). The alignment confirmed the presence of the conserved domains characteristic of this gene family (Apfel et al., supra).

Figure 1:
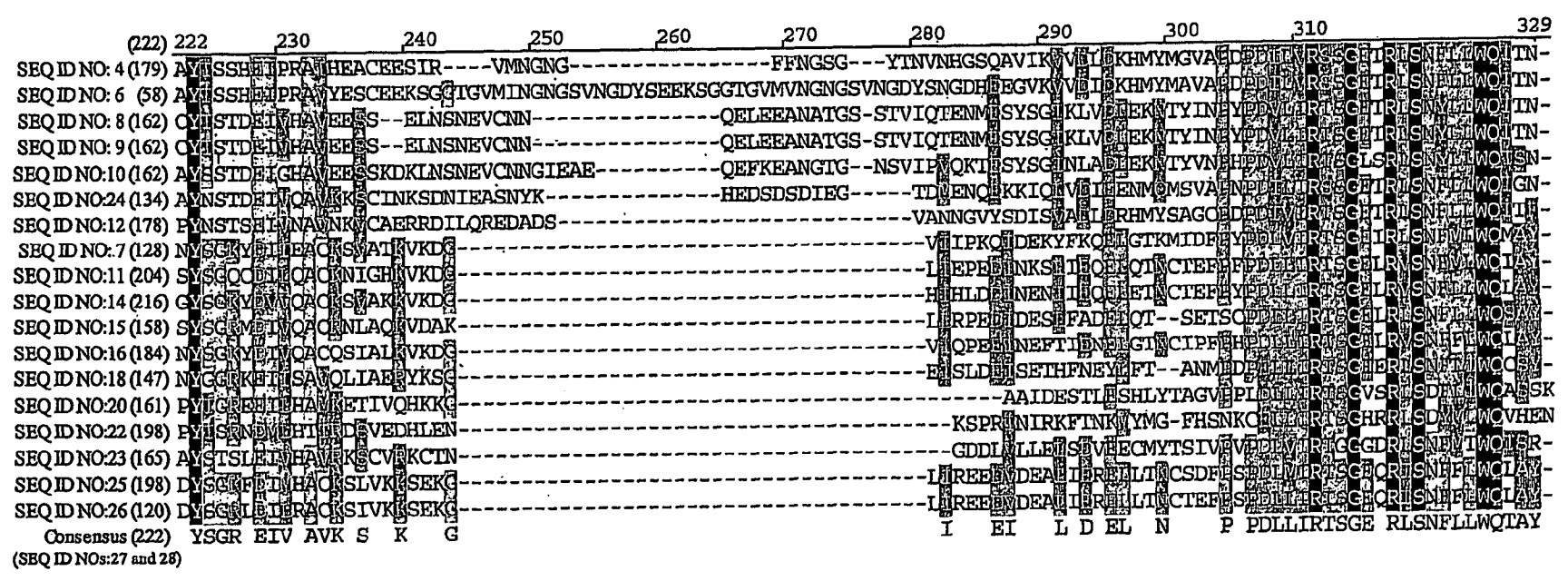

A portion of the alignment is shown in FIG. 1, corresponding to the region between Domain IV and V. This region defines a non-conserved domain indicative of the subfamily of cis-prenyltransferases associated with rubber-producing plants. Specifically, the domain comprises a sequence of non-conserved amino acids present between Domains IV and V, wherein the presence of the domain results in more than 50 amino acid residues being present between the absolutely conserved tyrosine of Domain IV and the first of the absolutely conserved arginine residues of Domain V. This is the first sequence feature to emerge as diagnostic for cis-prenyltransferases from rubber-producing plants, as there had not been enough proteins from such species characterized prior to this discovery to be able to identify such distinguishing feature(s).

Interestingly, SEQ ID NO:24, an Arabidopsis cis-prenyltransferase genomic clone of unknown function, alone of the non-rubber-producing species, contains a similar insert to the identified non-conserved domain of the present invention. This gene in Arabidopsis may thus represent a homolog of cis-prenyltransferases involved in rubber production present in the genome of this species.

Additionally, a cis-prenyltransferase protein from a rubber-producing plant can be identified by the presence of the conserved domains of amino acid sequences as follows:

|  |  | (SEQ ID NO:38) |
|---|---|---|
| Domain I | AFI(L/M)DGNRRFA | |
|  |  | (SEQ ID NO:39) |
| Domain IV | Y(T/S)SXX(D/E)IXXA | |
|  |  | (SEQ ID NO:40) |
| Domain V | PXPD(I/V)L(I/V)R(S/T)SG(E/L)(S/T)RLSNXLLWQ | | where these three domains occur sequentially in the order I, IV, V within the amino acid sequence and X may be any amino acid. These domains are essentially those recognized previously in bacterial sequences (Apfel, et al. supra), but have been modified to account for the differences observed in alignments of sequences of cis-prenyltransferases derived from plants (WO 01/21650).

Example 5

Expression Analysis of the Russian Dandelion Cis-prenyltransferase

This example describes work performed to examine the expression of the russian dandelion cis-prenyltransferase in leaf, root, scape and latex tissues. As expected, the protein is expressed predominantly in tissues known to accumulate rubber in this species (i.e., in the rubber-containing latex).

RNA was prepared from the leaf, root and scape of russian dandelion, using the RNAeasy Midi-Kit (Qiagen, Valencia, Calif.) for samples from plant tissue. RNA from russian dandelion latex was prepared as decribed by Kush, et. al. (Proc. Natl. Acad. Sci. 87:1787–1790 (1990)). 10 μg of total RNA from russian dandelion latex, leaf, root, and scape was denatured on a formadelhyde gel, using products and the supplied protocol from 5' to 3', Inc. (Boulder, Colo.). The gel was rinsed twice in 20×SSC for 15 min and then transferred to a nylon membrane (Roche Applied Science, Indianapolis, Ind.) by capillary action at 4° C. overnight. The RNA was then crosslinked to the membrane using a UV crosslinker (Stratagene, La Jolla, Calif.).

A digoxigenin (DIG) labeled russian dandelion cis-prenyltransferase EST fragment was synthesized, using the PCR DIG Probe Synthesis Kit (Roche Applied Science, Indianapolis, Ind.) and the following oligionucleotides: Dan5 (SEQ ID NO:41) and Dan6 (SEQ ID NO:42). This probe was then hybridized to the membrane and detected using the DIG Wash and Block Buffer Set (Roche Applied Science, Indianapolis, Ind.). The membrane was then exposed to BioMax Scientific Imaging Film (Eastman Kodak Co., Rochester, N.Y.) for 20 min. As shown in FIG. 2A, cis-prenyltransferase expression was detected in the root (lane A), scape (lane B) and latex (lane C) tissues, with the highest level of expression detected in latex. Little or no expression of cis-prenyltransferase was detected in the leaf tissue (lane D).

The membrane was then stripped of the DIG labeled russian dandelion cis-prenyltransferase probe by washing it in boiling 0.1% SDS for 10 min, followed by 1× Washing Buffer from the DIG Wash and Block Buffer Set for 5 min. A digoxigenin (DIG) labeled russian dandelion ubiquitin probe was synthesized, using the DIG DNA labeling Kit, according to the supplied protocol (Roche Applied Science). This probe was then hybridized to the membrane, detected using the DIG Wash and Block Buffer Set, and the membrane was exposed to BioMax Scientific Imaging Film (20 min).

Ubiquitin expression was detected in all tissues (FIG. 2B). Assuming that ubiquitin is equally expressed in all russian dandelion tissues, the amount of leaf (lane D), latex (lane C) and root (lane A) RNA loaded onto the gel was approximately equal while slightly more scape (lane B) RNA was loaded. It is clear from this analysis that the dandelion cis-prenyltransferase gene is expressed predominantly in tissues known to accumulate rubber in this species, and in particular in the rubber-containing latex. Thus, there is a clear association between this gene product and rubber biosynthesis.

Example 6

Cloning of a Partial cDNA Sequence of the Russian Dandelion Cis-prenyltransferase Gene Using Synthetic Oligonucleotide Primers in Reverse-transcriptase PCR This Example serves to confirm the presence of a transcript of the cloned cis-prenyltransferase gene in latex of russian dandelion, as indicated in the proceeding examples. It also demonstrates how synthetic oligonucleotide primers designed using gene sequences of plant cis-prenyltransferases may be used to clone additional cis-prenyltransferase genes from other species.

SEQ ID NOs:8–10, respresenting the Hevea Hpt1, Hpt2 and Hpt3 proteins were aligned using Vector NTI. A degenerate sense primer was designed to a region of high conservation (SEQ ID NO:43). Then, the following amino acid sequences were aligned in Vector NTI: SEQ ID NOs:7–10 and 12–16, representing the cis-prenyltransferase proteins from Hevea, pot marigold, rice, soybean, wheat, and the african daisy. A degenerate antisense primer was designed to a region of high conservation (SEQ ID NO:44).

RT-PCR was performed on total russian dandelion latex RNA with these primers (SEQ ID NOs:43 and 44), using Platinum PCR SuperMix (Invitrogen, Carlsbad, Calif.). The resulting RT-PCR products were TA-cloned, using the pGEM-t Easy Vector System (Promega Corp., Madison, Wis.) and the resulting plasmids were transformed into E. coli. Plasmids were isolated and purified using QIAFilter cartridges (Qiagen, Valencia, Calif.). Sequences were generated on an ABI Automatic sequencer using dye terminator technology, using a combination of vector-specific primers, and sequence editing was performed in Vector NTI.

The nucleotide sequences of the RT-PCR products were aligned with nucleotide sequences of known plant cis-prenyltransferase genes (Table 1). One 799 bp RT-PCR product (clone #4-4) showed significant homology to the known cis-prenyltransferase genes. The deduced amino acid sequence of this RT-PCR product (SEQ ID NO:45) was aligned with the deduced amino acid sequences of the known plant cis-prenyltransferase proteins as well as the amino acid sequence of the undecaprenyl diphosphate synthase (UPPS) protein and was determined by homology to be a russian dandelion homolog of UPPS.

Example 7

Comparison of Rubbers Prepared from Different Rubber-producing Plant Species This Example compares the properties of natural rubber prepared from russian dandelion, Hevea, sunflower and guayule.

The roots of 5 russian dandelion plants were cut off at the point where leaves emerged, and latex which seeped out of the cut roots was collected, yielding 200 mg latex. After stirring overnight in toluene (10 ml), the preparation was extracted with water in a separating funnel and the rubber precipitated from the organic phase by addition of an equal volume of methanol. After redissolving in toluene, methanol precipitation was repeated a further two times to purify the rubber. A total of 49.3 mg rubber was thus obtained, which was dissolved in toluene for analysis.

Hevea and guayule (P. argentatum) washed rubber particles were prepared essentially according to previously published procedures (Cornish, K., et al. J. Natural Rubber Res. 8:275–285 (1993); Cornish, K., and Backhaus, R. Phytochemistry 29: 3808–3813 (1990)). Rubber was extracted into toluene and, after washing with water, precipitated three times with methanol as described above. From 274 mg guayule rubber particles, 45.6 mg rubber was obtained; and from 303.8 mg Hevea rubber particles, 50.8 mg rubber was obtained.

Sunflower rubber was prepared by extraction of freeze-dried leaf material in a Soxhlet apparatus first with acetone and then with hexane. To the hexane extract, an equal volume of methanol was added to precipitate the rubber. The precipitate was collected by filtration onto glass fiber filters, and after allowing solvent to evaporate, redissolved in toluene. Methanol precipitation from toluene was repeated three times. From 27.7 g leaf dry weight, 5.1 mg rubber was obtained.

To determine molecular weight, samples of rubber (dissolved in toluene) were subjected to gel permeation chromatography on PLGel columns (Polymer Laboratories, Amherst, Mass.) calibrated with polystyrene standards (Polymer Laboratories). Tetrahydrofuran (THF) was used as eluent, and refractive index and UV absorbtion were monitored.

Data obtained from these analyses (Table 3) show that rubber extracted from these 4 species exhibit marked differences in molecular weight and molecular weight distribution (MWD), or polydispersity. The large degree of polydispersity in the rubber of Hevea is due to the presence of two distinct peaks in the chromatogram, as has previously been observed (Subramanian, A. Gel Permeation Chromatography of Natural Rubber. In, Rubber Chemistry & Technology March 1972; pp. 346–358). In contrast, the rubbers of russian dandelion, sunflower and guayule are monodisperse.

The rubber obtained from russian dandelion exhibited a higher weight average molecular weight (MW) than that of Hevea, while sunflower rubber was of considerably lower molecular weight, in accordance with previous observations (Seiler, G. J., et al., Economic Botany 45: 4–15 (1991)). This molecular weight of sunflower is close to the molecular weight desired for an 'ideal' liquid natural rubber (LNR), which would have the following properties (Nor, H. M., and Ebdon, J. R. Progress in Polymer Science 23: 143–177 (1998)):

A weight average molecular weight (Mw) of <80,000;
A number average molecular weight (Mn) of <50,000;
A MWD (determined as Mw/Mn) of <4.0; and
An intrinsic viscosity (IV) of 0.2–0.5.

TABLE 3

Gel Permeation Chromatography analysis of plant rubbers

| PLANT SPECIES | MW[1] | MN[2] | MWD[3] | IV[4] |
|---|---|---|---|---|
| H. brasiliensis | $1.44 \times 10^6$ | 252,689 | 5.71 | 7.35 |
| H. annus | 68,998 | 33,134 | 2.08 | 0.671 |
| P. argentatum | $1.47 \times 10^6$ | 641,640 | 2.3 | 7.719 |
| T. kok-saghyz | $2.18 \times 10^6$ | $1.21 \times 10^6$ | 1.8 | 10.633 |

[1]Weight average molecular weight
[2]Number average molecular weight
[3]MW/MN
[4]Intrinsic viscosity As expected from previous studies, different rubbers from different species can display marked differences in their fundamental properties of molecular weight, polydispersity, and intrinsic velocity. These factors must be considered during the development of alternative commercial rubber sources to Hevea, and are likely to be influenced by the specific cis-prenyltransferase enzymes involved in their polymerization.

What is claimed is:

1. An isolated nucleic acid molecule encoding a cis-prenyltransferase enzyme, selected from the group consisting of:
   a) an isolated nucleic acid molecule encoding the amino acid sequence as set forth in SEQ ID NO:4;
   b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or
   an isolated nucleic acid molecule that is fully complementary to (a) or (b).

2. An isolated nucleic acid molecule as set forth in SEQ ID NO: 3.

3. An isolated nucleic acid molecule comprising a first nucleotide sequence encoding a polypeptide of at least 301 amino acids that has at least 90% identity based on the Smith-Waterman method of alignment when compared to a polypeptide having the sequence as set forth in SEQ ID NO:4 or a second nucleotide sequence comprising the complement of the first nucleotide sequence, wherein said polypeptide has cis-prenyltransferase activity.

4. A recombinant DNA construct comprising the isolated nucleic acid molecule of claim 1 operably linked to suitable regulatory sequences.

5. A transformed host cell comprising the isolated nucleic acid molecule of claim 1.

6. The transformed host cell of claim 5 wherein the host cell is selected from the group consisting of plant cells and microbial cells.

7. A host cell according to claim 6 selected from the group consisting of russian dandelion (*Taraxacum kok-saghyz*), rubber tree (*Hevea brasiliensis*), guayule (*Parthenium argentatum*), sunflower (*Helianthus* spp.), tobacco (*Nicotiana* spp.), tomato (*Lycopersicon* spp.), potato (*Solanum* spp.), hemp (*Cannabis* spp.), sorghum (*Sorghum vulgare*), wheat (*Triticum* spp.), maize (*Zea mays*), rice (*Oryza sativa*), rye (*Secale cereale*), oats (*Avena* spp.), barley (*Hordeum vulgare*), rapeseed (*Brassica* spp.), broad bean (*Vicia faba*), french bean (*Phaseolus vulgaris*), other bean species (*Vigna* spp.), lentil (*Lens culinaris*), soybean (*Glycine max*), arabidopsis (*Arabidopsis thaliana*), cotton (*Gossypium hirsutum*), petunia (*Petunia hybrida*), flax (*Linum usitatissimum*) and carrot (*Daucus carota sativa*).

8. The transformed host cell of claim 6 wherein the host cell is selected from the group consisting of *Aspergillus*, *Saccharomyces*, *Pichia*, *Candida*, *Hansenula*, *Bacillus*, *Escherichia*, *Salmonella* and *Shigella*.

* * * * *